(12) United States Patent
Gardner

(10) Patent No.: US 7,225,183 B2
(45) Date of Patent: May 29, 2007

(54) ONTOLOGY-BASED INFORMATION MANAGEMENT SYSTEM AND METHOD

(75) Inventor: Steve Gardner, Royston (GB)

(73) Assignee: IPXL, Inc., Mountain View, CA (US)

( * ) Notice: Subject to any disclaimer, the term of this patent is extended or adjusted under 35 U.S.C. 154(b) by 209 days.

(21) Appl. No.: 10/352,197

(22) Filed: Jan. 28, 2003

(65) Prior Publication Data

US 2003/0177112 A1    Sep. 18, 2003

Related U.S. Application Data

(60) Provisional application No. 60/366,236, filed on Mar. 22, 2002, provisional application No. 60/351,378, filed on Jan. 28, 2002, provisional application No. 60/351,379, filed on Jan. 28, 2002, provisional application No. 60/351,380, filed on Jan. 28, 2002.

(51) Int. Cl.
*G06F 17/30* (2006.01)

(52) U.S. Cl. ............. 707/3; 707/2; 707/10; 707/104.1; 704/4; 704/9

(58) Field of Classification Search ............. 707/2, 707/3, 10, 104.1; 704/4, 9, 257; 706/45, 706/50; 717/144
See application file for complete search history.

(56) References Cited

U.S. PATENT DOCUMENTS

| | | | | |
|---|---|---|---|---|
| 4,270,182 A | * | 5/1981 | Asija | 704/8 |
| 4,864,502 A | * | 9/1989 | Kucera et al. | 704/8 |
| 4,887,212 A | * | 12/1989 | Zamora et al. | 704/8 |
| 4,914,590 A | * | 4/1990 | Loatman et al. | 704/8 |
| 4,984,178 A | * | 1/1991 | Hemphill et al. | 704/255 |
| 5,056,021 A | * | 10/1991 | Ausborn | 704/9 |
| 5,237,502 A | * | 8/1993 | White et al. | 704/1 |
| 5,309,359 A | * | 5/1994 | Katz et al. | 707/102 |
| 5,331,556 A | * | 7/1994 | Black et al. | 704/9 |
| 5,933,822 A | * | 8/1999 | Braden-Harder et al. | 707/5 |
| 5,953,727 A | | 9/1999 | Maslyn et al. | 707/104 |
| 5,966,712 A | | 10/1999 | Sabatini et al. | 707/104 |
| 5,970,500 A | | 10/1999 | Sabatini et al. | 707/104 |
| 6,021,387 A | * | 2/2000 | Mozer et al. | 704/232 |
| 6,023,659 A | | 2/2000 | Seilhamer et al. | 702/19 |
| 6,026,388 A | * | 2/2000 | Liddy et al. | 707/1 |
| 6,049,799 A | * | 4/2000 | Mangat et al. | 707/10 |
| 6,055,531 A | * | 4/2000 | Bennett et al. | 707/5 |

(Continued)

FOREIGN PATENT DOCUMENTS

WO    WO 01/15042    3/2001

(Continued)

OTHER PUBLICATIONS

Goble, Professor Carole, "Supporting Web Based Biology with Ontologies", *Information Technology Applicaions in Biomedicine*, Oct. 9-10, 2000, pp. 384-389.

(Continued)

*Primary Examiner*—Shahid Alam
(74) *Attorney, Agent, or Firm*—Roberts Mlotkowski & Hobbes

(57) ABSTRACT

An information management system and method is provided for integrating structured and unstructured data using an ontological approach, and further comprises processes for creating, validating, augmenting, and combining ontologies for life science informatics and other disciplines.

26 Claims, 20 Drawing Sheets

U.S. PATENT DOCUMENTS

| | | | |
|---|---|---|---|
| 6,076,051 A * | 6/2000 | Messerly et al. | 704/9 |
| 6,125,383 A | 9/2000 | Glynias et al. | 709/202 |
| 6,185,561 B1 | 2/2001 | Balaban et al. | 707/6 |
| 6,189,013 B1 | 2/2001 | Maslyn et al. | 707/104 |
| 6,223,186 B1 | 4/2001 | Rigault et al. | 707/104 |
| 6,229,911 B1 | 5/2001 | Balaban et al. | 382/128 |
| 6,233,575 B1 * | 5/2001 | Agrawal et al. | 707/6 |
| 6,263,287 B1 | 7/2001 | Zheng et al. | 702/20 |
| 6,675,159 B1 * | 1/2004 | Lin et al. | 707/3 |
| 7,027,974 B1 * | 4/2006 | Busch et al. | 704/4 |

FOREIGN PATENT DOCUMENTS

| | | |
|---|---|---|
| WO | WO 02/10980 | 2/2002 |

OTHER PUBLICATIONS

Baker, Patricia G., et al., "An Ontology for Bioinformatics Applications", *Bioinformatics*, vol. 15, No. 6, Jun. 1999, pp. 510-520.

Goble, C. A., et al., "Transparent Access to Multiple Bioinformatics Information Sources", *IBM Systems Journal*, vol. 40, No. 2, 2001, pp. 532-551.

Lambrix, Patrick, et al., "Evaluation of Ontology Development Tools for Bioinformatics", *Bioinformatics*, vol. 19, No. 12, 2003, pp. 1564-1571.

Hwang, Chung Hee, "Incompletely and imprecisely Speaking: Using Dynamic Ontologies for Representing and Retrieving Information", Microelectronics and Computer Technology Corporation, © 1999, 4 pages.

* cited by examiner

ONTOLOGY-BASED INFORMATION MANAGEMENT SYSTEM AND METHOD

CROSS-REFERENCE TO RELATED APPLICATIONS

This application claims priority to U.S. Provisional Patent Application Ser. No. 60/351,378, filed Jan. 28, 2002; U.S. Provisional Patent Application Ser. No. 60/351,379, filed Jan. 28, 2002; U.S. Provisional Patent Application Ser. No. 60/351,380, filed Jan. 28, 2002; and U.S. Provisional Patent Application Ser. No. 60/366,236, filed on Mar. 22, 2002, each of which are incorporated by reference in their entirety.

The following U.S. Patent Applications, filed contemporaneously herewith, are specifically and entirely incorporated herein by reference: (1) U.S. patent application Ser. No. 10/352,246 filed Jan. 28, 2003, titled "Bioinformatics System Architecture with Data Process Integration for Overall Process Management;" (2) U.S. patent application Ser. No. 10/352,242 filed Jan. 28, 2003, titled "Modular Bioinformatics Platform;" and (3) U.S. patent application Ser. No. 10/352,196 filed Jan. 28, 2003, titled "User Interface for a Bioinformatics System."

FIELD OF THE INVENTION

This invention relates generally to information management, and more particularly to an ontology-based information management system and method that integrates structured and unstructured data using an ontological approach, and further comprises processes for creating, validating, augmenting, and combining ontologies for life science informatics and other disciplines.

BACKGROUND OF THE INVENTION

An ontology may be broadly interpreted as a dynamic, controlled vocabulary for describing a plurality of objects or concepts contained in a process or domain, and their interrelationships. An ontology may be further thought of as a formal knowledge-representation system which comprises rules for encoding the manner in which knowledge is represented, along with rules that enable automated reasoning with regard to the objects or concepts represented.

An ontology term may be a single named concept describing an object or entity. A concept may, for example, comprise a collection of words and associated relevance weights, co-occurrence and word localization statistics that describe a topic.

In various disciplines, scientific or otherwise, a number of resources (e.g., data management systems) may exist for representing cumulative knowledge gathered for different specialty areas within each discipline. Some existing systems, for instance, may use separate ontologies for each area of specialty within a particular discipline. One drawback associated with such ontology systems, however, is the inability to link different areas of specialty within a discipline.

Another drawback associated with existing ontology systems is the inability to map ontology terms to infer linkages to related or referenced entities in wider data sources.

Moreover, while existing ontology systems generally offer descriptions of a particular discipline syntactically (in terms of nouns or entity names), they often lack a particularly well-developed set of semantic relationships (in terms of verbs or relationship between entities) built into the ontology.

Yet another drawback associated with existing ontology systems is a general lack of names in an ontology that correspond to all the information or concepts in a document set. For example, in existing systems, ontologies are often specific to a few sub-domains, and to the data sources that are relevant to those sub-domains. For example, in a life science system, a gene ontology (GO) may deal with objects that are related to cellular locations, biological processes, and molecular functions, while potentially missing a number of other aspects or objects relevant to a particular life science domain. This may create potential "completeness" issues if the gene ontology was alone used to represent all of the information in a document set pertaining to the life science domain.

In existing systems, the ontology for each sub-domain may be populated unevenly. Some sub-domains (representing an area of active research) may be relatively well populated when compared to other sub-domains. Additionally, even within a sub-domain, differing levels of detail are often provided. Some areas may be relatively well-defined and comprise easily discriminated concepts, while other areas may not. Existing systems do not address evaluating the levels of specificity and how discriminating terms in an ontology may be.

In life science disciplines, for example, many ontology terms have not been tested against any current database, particularly in information content and retrieval terms. In addition, many of the terms do not have any references to external databases. This may result in a user not knowing beforehand whether it is possible to discriminate between any pair of terms based on the available evidence for those terms and the availability and/or capability of information retrieval (IR) tools. If a user cannot discriminate between a pair of terms using existing information retrieval tools, the terms may effectively be treated as one in the same. As such, another drawback in existing ontology systems is the apparent inability to generate the maximally diverse set of discriminable terms that may be derived from a starting ontology.

Yet another drawback in existing ontology systems is the apparent inability to discover a new set of terms that describe identifiable, discriminable concepts in the rest of an information space.

Still yet another drawback associated with existing ontology systems is the apparent inability to evaluate the distance between a pair of ontology terms.

Further, existing systems deal with information that may be inherently represented by terms in an ontology. This begs the question, "What happens if information exists that has not been codified in an ontology?" There is a great deal of information space that unfortunately may not be fully described by terms in existing ontologies.

These and other drawbacks exist.

SUMMARY OF THE INVENTION

The invention solving these and other problems relates to an ontology-based information management system and method that integrates structured and unstructured data using an ontological approach, and further comprises processes for creating, validating, augmenting, and combining ontologies for life science informatics and other disciplines.

According to an embodiment of the invention, an ontology may be used to enable effective syntactic and semantic mapping between entities discovered using concept-based text searching, and those derived from data warehousing and mining in a plurality of disciplines (e.g., life sciences).

According to an embodiment, the invention uses an ontology to provide semantic mapping between entries in a structured data source, and concepts in an unstructured data source.

According to a further embodiment of the invention, processes for validating and augmenting an ontology may be provided. These processes may include operations such as, for example, computing a distance matrix for a given set of ontology terms measured against a specific document, validating terms in a given ontology against specific document sets, combining multiple available ontologies, augmenting an existing ontology with new terms, and validating a scope of a given ontology.

According to an embodiment, the invention may evaluate the distance between a pair of terms in a given information space using an Information Retrieval (IR) engine capable of categorizing large document sets. Such distances may be quantified and visualized using hierarchical map displays.

According to an embodiment, the invention may augment ontologies by creating new ontologies for information that had previously never been codified in an ontology. In some embodiments, the ontologies may be augmented according to a plurality of user-enabled formulas.

The features and functionality of the system and method of the invention, as disclosed herein, may be utilized in a wide variety of contexts, and within a single domain, across multiple domains, within a sub-domain, or any other combination of domains or portions thereof.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF PREFERRED EMBODIMENTS

Figure 1:
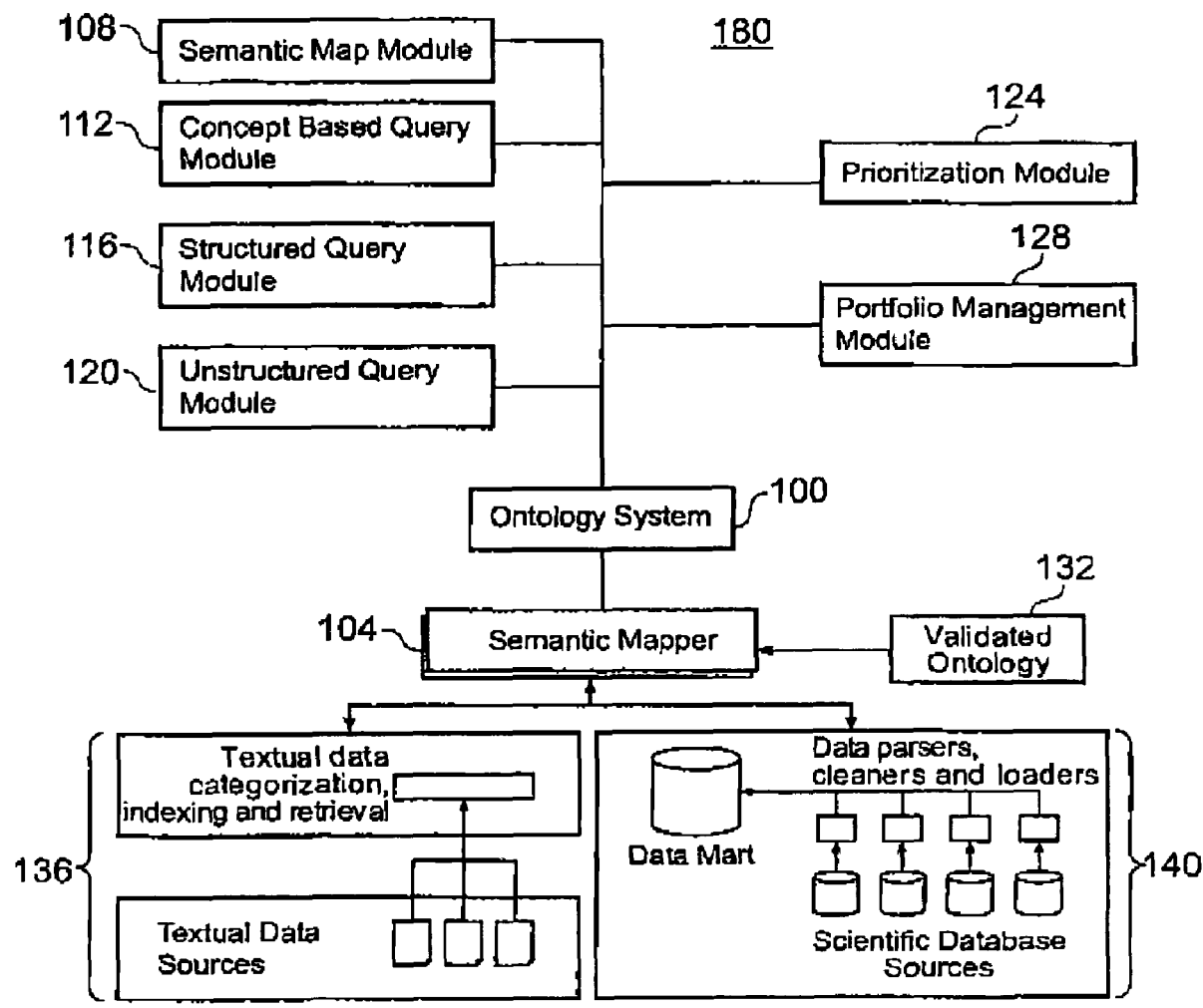
FIG. 1 illustrates a system architecture, according to an embodiment of the invention.

An embodiment of the invention relates to an ontology-based information management system and method that integrates structured and unstructured data using an ontological approach, and further comprises processes for creating, validating, augmenting, and combining ontologies for life science informatics and other disciplines.

According to an embodiment, the invention may use an ontology (e.g., genomics) to provide semantic mapping between entries in, for example, a structured data mart and concepts in unstructured textual documents. The invention may map information from multiple sources to a common ontology, which may reduce a number of data transformation steps often required to integrate data. Mapping information to a common ontology may also enable various data or other applications to access data in a consistent way. As an illustrative example, the system of the invention may semantically map structured information from existing genomics, proteomics, screening, and chemistry databases, with unstructured textual (or other) data from intellectual property (e.g., patent) databases, project documents, scientific literature, or any other unstructured data sources.

An ontology, in accordance with the invention, may describe entities in a domain both syntactically (in terms of nouns, or entity names), and semantically (in terms of verbs, or relationships between entities).

An ontology may be used to enable effective syntactic and semantic mapping between any number of different entities, including, but not limited to, entities discovered using concept-based text searching, and those derived from data warehousing and mining in a plurality of disciplines (e.g., life science informatics). For example, many relationships between entities may be of the form "IS A," "HAS A," or "IS PART OF A." Illustrative examples may include: (1) "Tyrosine Kinase IS A Protein Kinase;" or (2) "A cell HAS A Nucleus." These examples represent very simple relationships that may fail to describe the richness of interactions occurring in a cellular or metabolic process.

A description, such as, for instance, "Alcohol Dehydrogenase IS UPREGULATED IN THE PRESENCE OF Alcohol," may facilitate a richer and more thorough description of a particular domain. This type of empirically-derived inference, however, may require synthesis from a plurality of experimental observations carried out by a plurality of research groups worldwide. The system and method of the invention enables such inferences to be derived based, in-part, on concept-based searching.

According to an embodiment of the invention illustrated in FIG. 1, a system 180 is provided comprising an ontology system 100 which may be coupled to a semantic mapper 104 to enable ontology-based searching using a context network (described in detail below).

According to an embodiment, a validated ontology or ontology 132 may be used to provide the semantic mapping between entries in a structured data source and concepts in unstructured data documents. In particular, semantic mapper 104 may map relational information between one or more structured data sources 140, and one or more unstructured data sources 136.

Unstructured data sources 136 may comprise, for example, unstructured textual (or other) data from intellectual property (e.g., patent) databases, project documents, product development documents, scientific literature, market-related information, or any other unstructured data sources. Information taken from unstructured data sources 136 may be retrieved using query engines, categorized using one or more statistical methods, indexed based on category, and stored in a second data source 144. According to an alternative embodiment, unstructured data sources 136 may comprise information that has already been categorized and indexed. Other configurations may be implemented, as would be apparent to those having skill in the art.

According to an embodiment of the invention, structured data sources 140 may comprise, for example, structured information from existing genomics, proteomics, screening, and chemistry databases, or structured data or information from any other database or data source. In some embodiments, structured data sources 140 may include one or more public databases (e.g., EMBL, Ensembl, KEGG, GenBank, etc.) as well as one or more proprietary databases (e.g., Celera Genomics). Other public or proprietary databases may be incorporated.

According to an embodiment, structured data may be parsed and cleaned using a user-enabled set of instructions, and stored in a datamart 148.

According to an embodiment of the invention, semantic mapper 104 may, for example, map contents of one or more unstructured data sources 136 with the contents of one or more structured data sources 140. In some embodiments, semantic mapper 104 may map an index of data in one or more unstructured data sources 136 with an index of data in one or more structured data sources 140.

According to one aspect of the invention, ontology system 100 may query and/or retrieve information from one or more data sources and present the information to a user according to a plurality of user-enabled formulae (not illustrated).

According to an embodiment of the invention, ontology system 100 may comprise, interface to, or operate in conjunction with one or more of a semantic map module 108, concept-based query module 112, structured query module 116, unstructured query module 120, prioritization module 124, and portfolio management module 128. One or more of the modules may be combined. Additional modules may be provided. For some purposes, not all modules may be necessary.

According to an embodiment, ontology system 100 system may include or otherwise access information from structured data sources 140 using structured query module 116. Structured query module 116 may also be used to parse, clean, and load data from structured data sources 140.

Ontology system 100 may further include or otherwise access information from unstructured data sources 136 using unstructured query module 120. Unstructured query module 120 may also categorize, parse, and retrieve data from unstructured data sources 136.

According to an embodiment, ontology system 100 may include or otherwise access context information from both structured data sources 140 and unstructured data sources 136 using concept-based query module 112. Concept-based query module 112 may also be used to retrieve context information from any individual database. Concept-based query module 112 may also facilitate the discovery of relationships between tokens in a set of documents. Examples of tokens may include, but are not limited to, words, word roots, phrases, or any other identifiable set of characters that may be the subject of a search. When tokens appear more frequently than expected in a document set, and particularly when closely associated in text, they may be identified as being "related," or relevant to one another. Concept-based query module 112 may, according to one embodiment, determine such associations.

According to an embodiment of the invention, semantic mapper 104 may enable the mapping of structured and unstructured data using semantic map module 108, and may comprise server side tools to enable the querying of a plurality of data resources. Semantic mapper 104 may also link ontology system 100 to a context navigator (described in detail below) for enabling novel associations to be made between information found in structured and unstructured data.

According to an embodiment of the invention, ontology system 100 may create relevant context networks that facilitate more innovative decisions. A prioritization module 124 may be used to prioritize context terms corresponding to a search term, according to user input. In some embodiments, prioritization module 124 may include, for example, gene prioritization and/or transcript profiling.

Ontology system 100 may comprise a portfolio management module 128 and project decision support modules (not illustrated) for creating and managing an ontology portfolio for a specific subject matter (e.g., cancer). In another embodiment, the invention may enable decision makers and analysts to manage and exploit life science (or other) information by providing novel inferences that lead to improved decision-making.

Those having skill in the art will appreciate that system 180 works with various system configurations. According to one embodiment, for example, ontology system 100, semantic mapper 104, semantic map module 108, concept-based query module 112, structured query module 116, unstructured query module 120, prioritization module 124, and portfolio management module 128 may all comprise an application.

According to one embodiment, the application may be a stand-alone software application run on a workstation (not illustrated), or may be incorporated into an existing software application. A workstation may comprise any one or more of, for example, a desktop computer, portable computer, PDA (personal digital assistant), network-enabled appliance, or other device. The workstation may further include a microprocessor such as an Intel x86-based device, a Motorola 68k or PowerPC™ device, a MIPS, Hewlett-Packard Precision™, or Digital Equipment Corp. Alpha™ RISC processor, a microcontroller or other general or special purpose device operating under programmed control. Moreover, the workstation may also run any known operating system, platform, or application such as, for instance, Microsoft Windows™ 95, 98, Millenium™, NT™, or 2000, Windows™ CE™, PalmOS™, Unix, Linux, Xenix, IBM AIX™, Hewlett-Packard UX™, OS/2™, BeOS™, MacOS™, Novell Netware™, Sun Microsystems Solaris™, Mach, Apache, or OpenStep™.

According to an alternative embodiment (not illustrated), a server may host the application, thus requiring a user at a workstation to access the server over a network (via a communications link) to use the application. The server may be or include, for instance, a workstation running any known operating system or platform. The network may include any one or more of, for instance, the Internet, an intranet, a PAN (Personal Area Network), a LAN (Local Area Network), a WAN (Wide Area Network), a SAN (Storage Area Network), a MAN (Metropolitan Area Network), or any other network. The communications link may include any one or more of, for instance, a copper telephone line, a Digital Subscriber Line (DSL) connection, a Digital Data Service (DDS) connection, an Ethernet connection, an Integrated Services Digital Network (ISDN) line, and an analog modem connection, as well as a cable modem connection, a wireless connection, or other connection.

The server may be also be operatively connected to the one or more unstructured data sources 136 and second data source 144, as well as the one or more structured data sources 140 and datamart 148. According to an embodiment of the invention, any of the databases or data sources referred to herein, including datamart 148, may be, include, or interface to, for example, the Oracle™ relational database sold commercially by Oracle Corporation. Other databases, such as Informix™, DB2 (Database 2) or other data storage or query formats, platforms, or resources such as OLAP (On Line Analytical Processing), SQL (Structured Query Language), a SAN (storage area network), Microsoft Access™ or others may also be used, incorporated, or accessed into the invention.

Although the features and functionality of the system and method of the invention are described below and illustrated using examples taken from the life sciences, it should be understood that the system and method of the invention may be used with any type of information or data.

Figure 2:
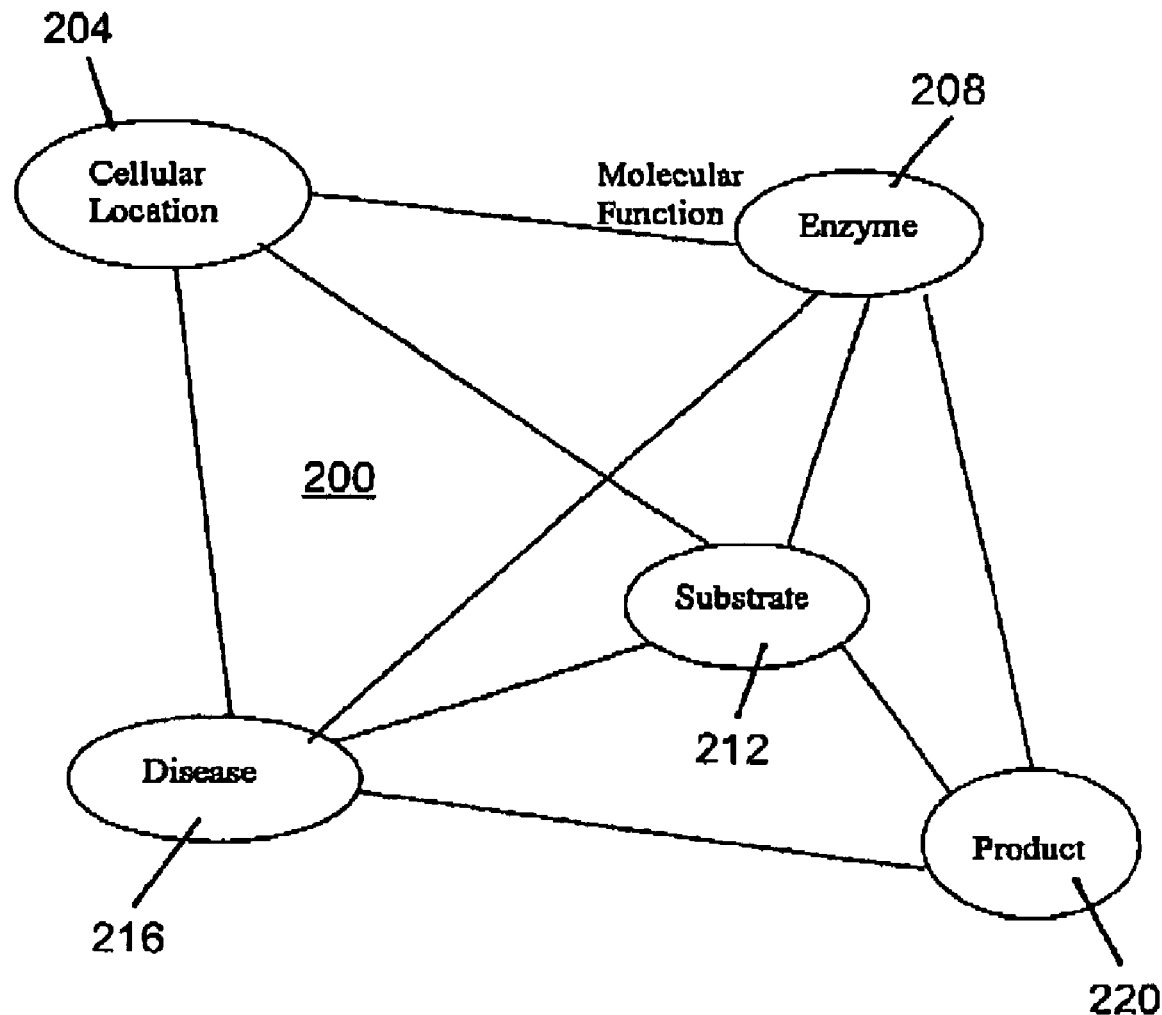
FIG. 2 illustrates an example of a context network, according to an embodiment of the invention.

According to an embodiment of the invention illustrated in FIG. 2 (and described in greater detail below), a context network 200 may result from an approach to structure knowledge within a specific information space that may be unique to a user's needs, whether it is a specific domain such as, for example, a disease area or therapeutic target, or a broader area such as genomics. A resulting validated "knowledge space" may allow concepts to form the basis for easy navigation to relevant data, both unstructured and structured, and the semantic linkages to make novel inferences from the data. This may create relevant context for information that may form the basis for better decisions. As such, the system and method of the invention may identify new trends and relationships in the data based on statistically relevant textual information, where much of the latent knowledge resides.

According to an embodiment of the invention, ontology system 100 may include, for example, a plurality of biological ontologies, wherein the ontologies may be stored in one or more domains, and wherein the one or more domains may be in a network. For example, as illustrated in FIG. 2, context network 200 may include a cellular location domain 204, enzyme domain 208, substrate domain 212, disease domain 216, and product domain 220.

Cellular location domain 204 may include, for instance, context-based ontologies corresponding to information related to cellular locations, such as, for example, location of a calmodulin-binding protein during various phases of cellular differentiation or cell cycles.

Enzyme domain 208 may include, for instance, context-based ontologies corresponding to information related to enzymes, such as, for example, the status of protease enzymes during calmodulin-dependent protein phosphorylation.

According to an embodiment, context information in cellular location domain 204 may be mapped to context information in enzyme domain 208. This functionality may enable a user to relate cellular location of calmodulin-biding proteins during calmodulin-dependent protein phosphorylation.

According to an embodiment, the context information in cellular location domain 204, enzyme domain 208, substrate domain 212, disease domain 216, and product domain 220 may be mapped to one another to provide context-based information from multiple domains to a user. A user may select one or more of these domains to obtain context-based information.

For example, the invention may enable a user to understand the coordination of morphological change in tissue samples with regard to the expression profiles of specific sets of genes in response to chemical stimuli using one or more biological ontologies. The user may touch a wide variety of chemical structure and sub-structure, gene sequence, gene expression, metabolic pathway, and tissue morphology resources in a plurality of biological ontology domains (not shown in figures). The invention may also ensure that a compound a user searches for in a sub-structure search, is the same as (or is contained in) compounds that may have been used in expression experiments. Furthermore, the invention may enable a user to understand in which pathways the genes whose expression levels are affected. A user may establish a mechanistic effect between the regulation of these pathways and the morphological change.

A user may ultimately be able to resolve the identity and relationships between multiple entities coming from chemistry, genomic, pathway, and experimental histopathology domains (not illustrated). Each of a plurality of domains may have its own ontology, and yet each may reference, for example, scientific, patent, or project literature sources (as well as any other sources) that may contain documentation of experiments performed and data associated with these entities. In some embodiments, the invention may enable a user to infer relationships by mapping ontology terms to these definitive sources, thereby enabling a user to establish new relationships that may have otherwise been impossible to prove.

Figure 3:
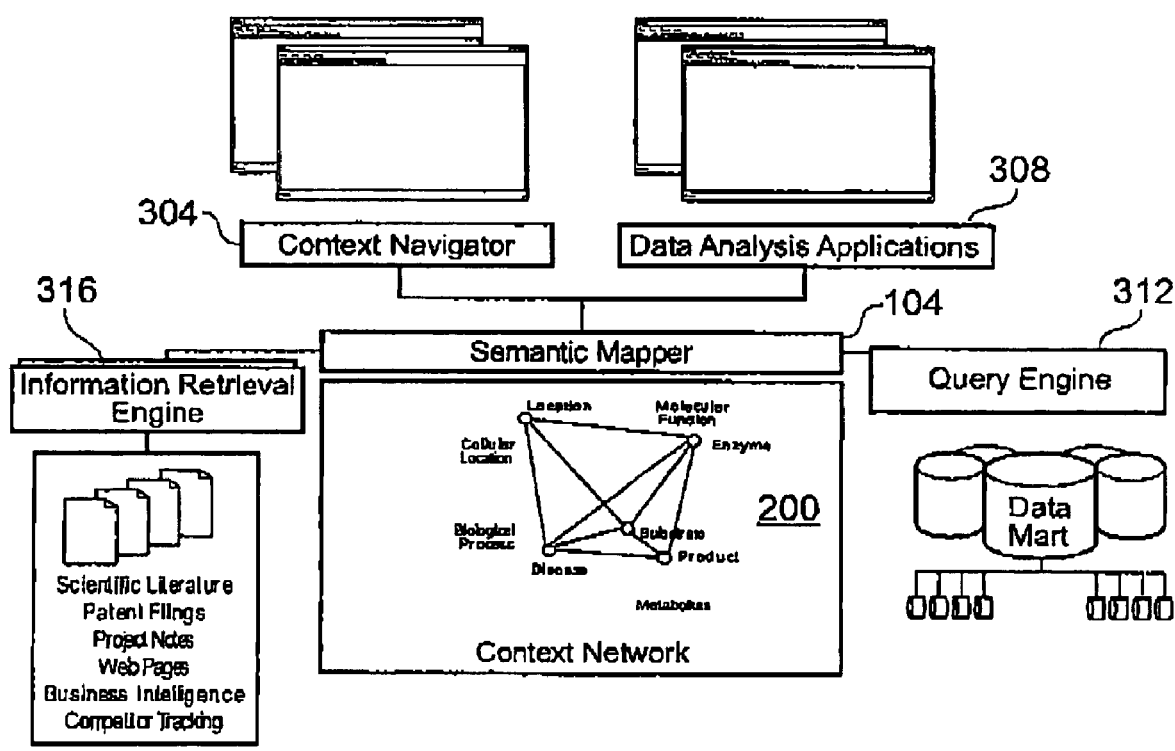
FIG. 3 illustrates a system architecture, according to an embodiment of the invention.

According to an embodiment of the invention illustrated in FIG. 3, the ontology and/or semantic mapping system of the invention may be integrated with one or more data analysis applications 308. For instance, ontology system 100 and semantic mapper 104 may be integrated with a third party application such as, for example, Spotfire's gene expressions data analysis system.

According to an embodiment, custom interfaces may be utilized to leverage the context network 200 and data resources. The ontology and/or semantic mapping system of the invention may be coupled to a context navigator 304 that may enable a user to navigate across one or more ontology domains.

According to one embodiment of the invention, functional components of semantic mapper 104 may include a structured query engine 312, and an unstructured information retrieval (IR) engine 316.

In one embodiment, structured query engine 312 may be a configurable XML query toolkit that may enable easy customizable searches to be performed against structured data. Query engine 312 may comprise a complete set of components that include descriptions of data resources and information on how they may be queried. Query engine 312 may enable rapid development and deployment of customizable user interfaces.

Unstructured IR engine 316 may provide semantic search and retrieval of text documents based on statistical language processing, and may also include some or all of the features of query engine 312 as described above.

Figure 4:
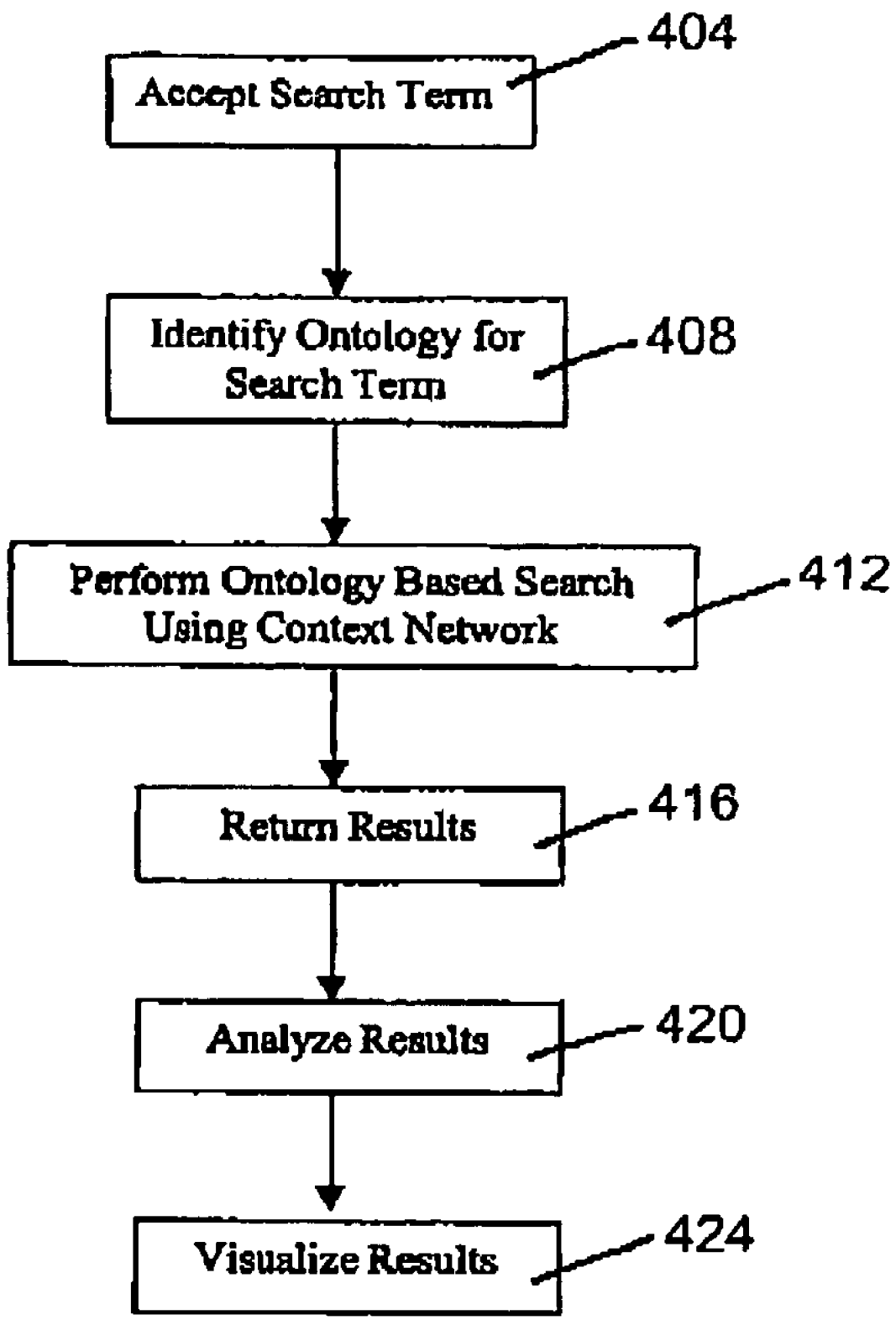
FIG. 4 illustrates a flowchart of processing according to the invention, in one regard.

FIG. 4 illustrates a flowchart of processing according to the invention, in one regard. In an operation 404, the system may accept one or more search strings from a user. In some embodiments, the system may accept one or more search strings of a plurality of languages. In other embodiments, the system may accept one or more search strings of a plurality of expressions (mathematical expressions) of characters.

In an operation 408, the system may identify ontologies for one or more accepted search strings. The system may perform one or more ontology-based searches, in operation 412, using a context network. The ontology-based searches may be performed according to one or more user-defined or user-selectable algorithms. According to an embodiment, the algorithms may correspond to a plurality of criteria for an ontology-based search including, for example, ontology domains and threshold level for matching contexts.

In an operation 412, search results may be returned to a user. Returned search results may be analyzed for further applications or activities in an operation 420.

According to an embodiment, returned search results may also be visualized, in an operation 424, using one or more modifiable viewing tools. In some embodiments, returned search results may be visualized using a hierarchical map, with a rooted tree based on relevancy to the one or more search strings.

According to one aspect of the invention, the system may recognize a user's personal background for an ontology-based search using a context network. For example, a user working in research and development may be interested in obtaining information relevant to research, while a user working in marketing may be interested in market-related information for a product.

Figure 5:
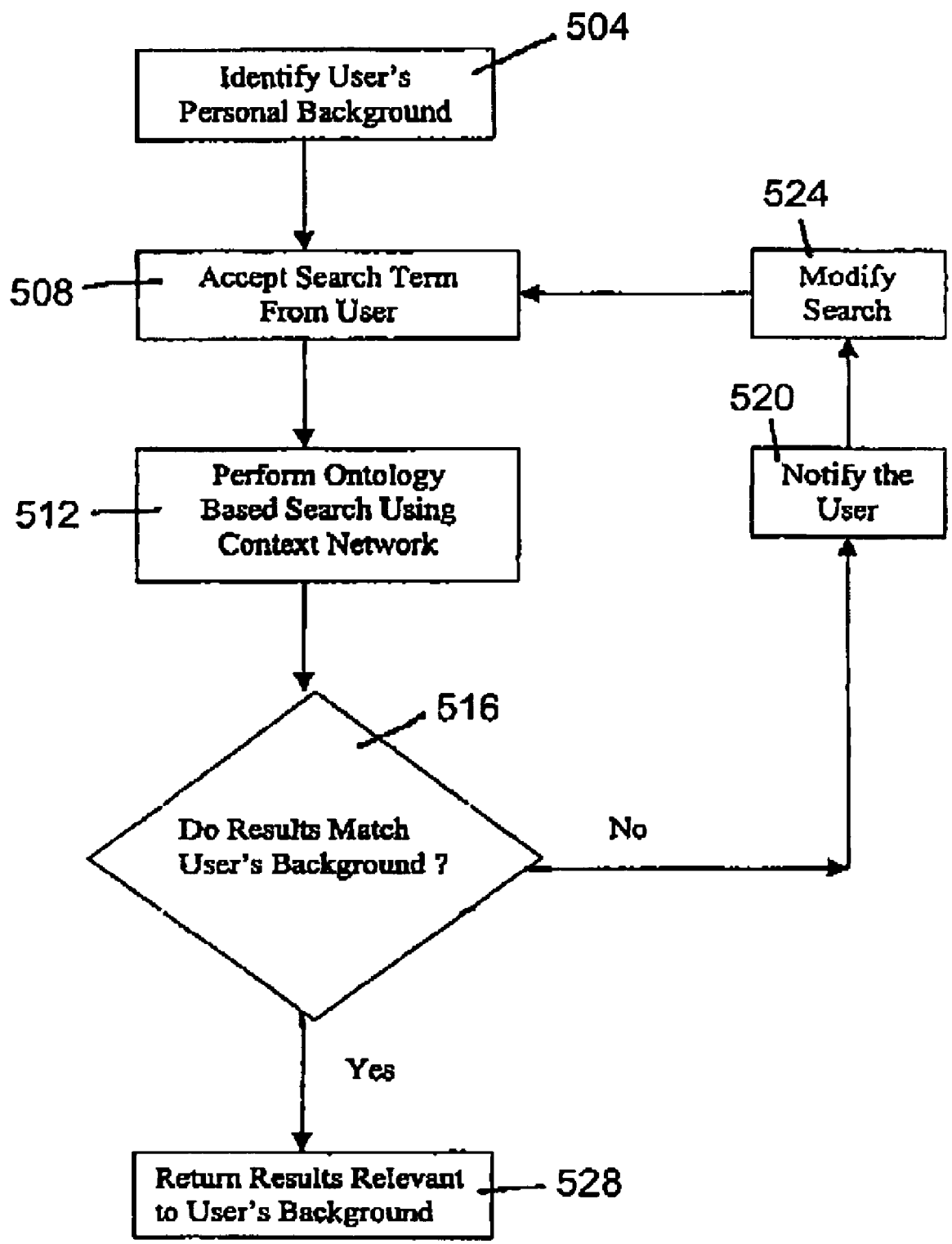
FIG. 5 illustrates a flowchart of processing according to the invention, in one regard.

FIG. 5 illustrates a flowchart of processing according to the invention, in one regard. In an operation 504, the system may identify a user's personal background (or user profile) information when a user access the system to initiate a session. In some embodiments, the system may automatically recognize a user's personal background (or user profile) information by accessing or "looking-up" the user's profile information from a networked system.

In an operation 508, the system may accept one or more search strings from the user. As recited above, in some embodiments, the system may accept one or more search strings of a plurality of languages. In other embodiments, the system may accept one or more search strings of a plurality of expressions (mathematical expressions) of characters.

In an operation 512, an ontology search may be performed using a context network and one or more user-selectable or user-defined algorithms.

According to an embodiment of the invention, the system may, in an operation 516, attempt to determine whether the search results of the ontology search match a user's personal background or personal profile. If the search results match a user's personal background or profile, the system may, in an operation 528, return results relevant to the user.

If, by contrast, the search results do not match a user's personal background or profile, the system may notify the user in an operation 520. The user may then modify one or more search strings to perform further ontology-based searching in an operation 524.

According to an embodiment, a user may instruct the system to ignore his/her personal background (or profile) and perform a random ontology-based search.

According to one embodiment, the system may extend beyond information retrieval (IR) tools with keyword and thesaurus-based systems, and provide users with relevant context-based information. For example, a typical search in scientific literature may involve multiple words (e.g., 'tyrosine kinase auto-catalysis') which may be combined into one search string.

Using an "AND" Boolean keyword search generally returns a set of documents containing only those exact keywords. Unfortunately, this approach (with a highly specific query) may not return highly relevant documents that may have mentioned protein kinases, or documents in which one or more of the words comprising the search string (e.g., auto-catalysis) have been misspelled. Any document that does not contain every keyword, has a misspelling, or an unknown alternate term may likely be missed.

Using an "OR" Boolean keyword search, on the other hand, may generate a huge list of articles containing one or more of the words, often returning perhaps hundreds or thousands of hits for common keywords. A user may have to sift through a sizeable list of search results just to try to find relevant information, and may often "give-up" in frustration.

One of the advantages of the invention is that the semantic mapping system provides relevant information based on users' needs because the invention is based, in-part, on the context of search terms. In some embodiments, the system may enable users to combine a context-based search with a Boolean key word search. In other embodiments, the system may perform the context-based search and Boolean search separately.

According to an embodiment, of the invention, a concept-based probabilistic search of the system may identify documents containing concepts that may be relevant to an inputted search term (e.g., tyrosine kinase mediated auto-catalysis) and return them while also classifying the types of documents into areas of relevance (e.g., clinical studies, molecular biology, metabolic pathways) for a given user. Probabilistic concept-based querying may attempt to assign relevance, domain knowledge, and structure to data being searched. The system may also seek out groups of tokens that, together, may infer concepts even when a query posed by a user is vague or ambiguous. This may ensure more accurate results than typical keyword-based search technologies as it does not simply search for exact term matches.

The system may, according to an embodiment, use a plurality of statistical measures to improve the relevance of the relationships discovered, including word localization, disambiguation, and categorization. In some embodiments, the system may use a knowledge of the structure and context of the contents of a document to improve the discrimination of the relevance of its contents to a particular topic.

Figure 6:
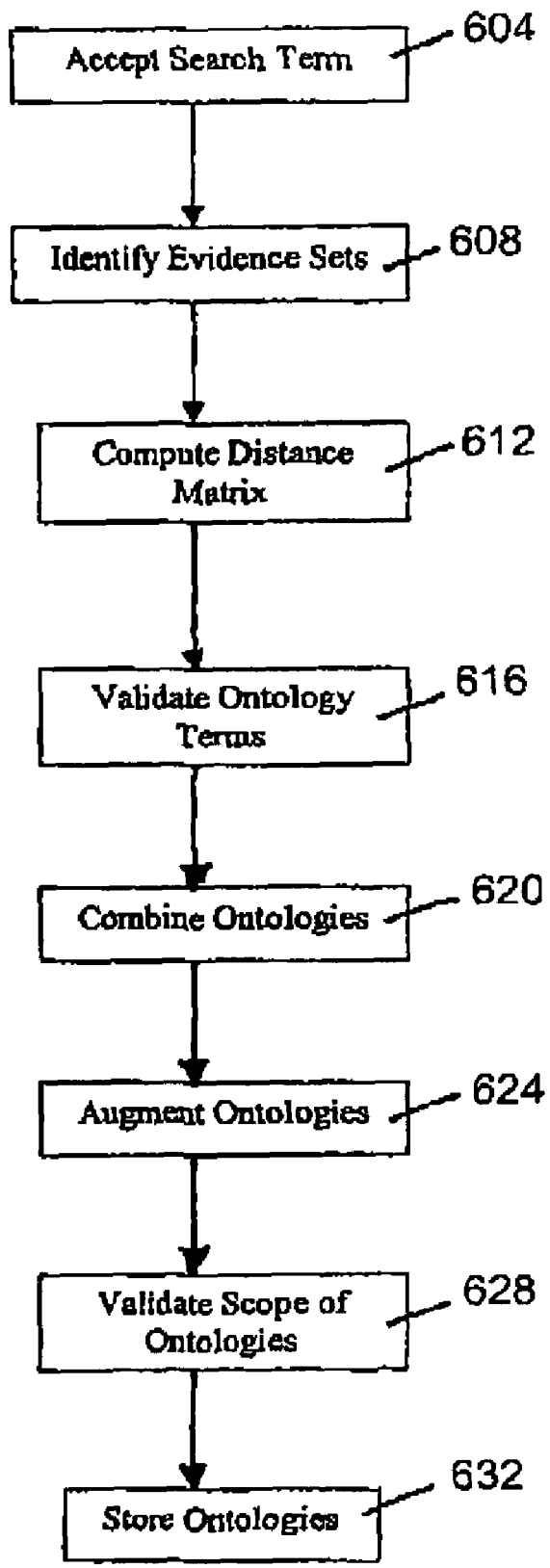
FIG. 6 illustrates a flowchart of processing according to the invention, in one regard.

According to one aspect of the invention, the system and method of the invention may be used for the creation, validation, augmentation, and combination of ontologies. FIG. 6 illustrates a flowchart of processing according to the invention, in one regard. In an operation 604, the system may accept one or more search strings of a plurality of characters for which a user may be interested in obtaining relevant information.

The system may identify, in an operation 608, one or more evidence sets for accepted search strings. In some embodiments, the system may parse the characters of the search terms for identification. In other embodiments, the system may recognize one or more sets of characters (e.g., a prefix) of a search term.

According to an embodiment of the invention, various aspects of a process for validating and augmenting an ontology may include a multitude of operations including, but not limited to, computing a distance matrix (operation 612), validating or filtering ontology terms (operation 616), combining ontologies (operation 620), augmenting ontologies (operation 624), validating the scope of an ontology (operation 628), and storing an ontology (operation 632).

In operation 612, a distance matrix computed for a given set of ontology terms may be measured against a specific document set. In operation 616, the system may validate the terms in a given ontology against specific document sets to establish a maximal set of ontology terms that may be discriminated with the available evidence sets. In operation 620, the system may combine multiple available ontologies into a single validated aggregate ontology. The system may, in operation 624, augment an existing ontology with newly discovered terms to maximize the discriminable term coverage. In some embodiments, an ontology may be augmented with newly discovered terms automatically based on a set of user enabled instructions.

In operation 628, the system may validate the scope of a given ontology against a specific document set to evaluate the extent of term coverage of the domain. In operation 632, an ontology may be stored.

According to an embodiment of the invention, a distance matrix may be a two (or more) dimensional array containing pair wise distances between ontology terms measured using different distance measures. A distance measure may include, for example, a metric used to evaluate the similarity or dissimilarity between two points in a given space. A variety of metrics may be used to describe similarity based on, for example, through node distance on a graph representation, through space distance on a cluster graph representation, or value difference when comparing multiple graphs or matrices.

According to one embodiment, the system may recognize the structure (e.g., the various headings—Introduction, Materials and Methods, Results, etc.) of documents. The system may further identify the contents of one or more structures of documents. In some embodiments, a keyword-based system may take all of the words, identify their position in a document, and create an inverted index listing the word against all of its' positions in the document. In other embodiments, the system may look for synonyms and near-terms, and may stem a word so that the root form may find all of its derivatives (e.g., "discover*" may return "discover," "discovery," "discoverer," "discovered," etc.).

Figures 7, 8:
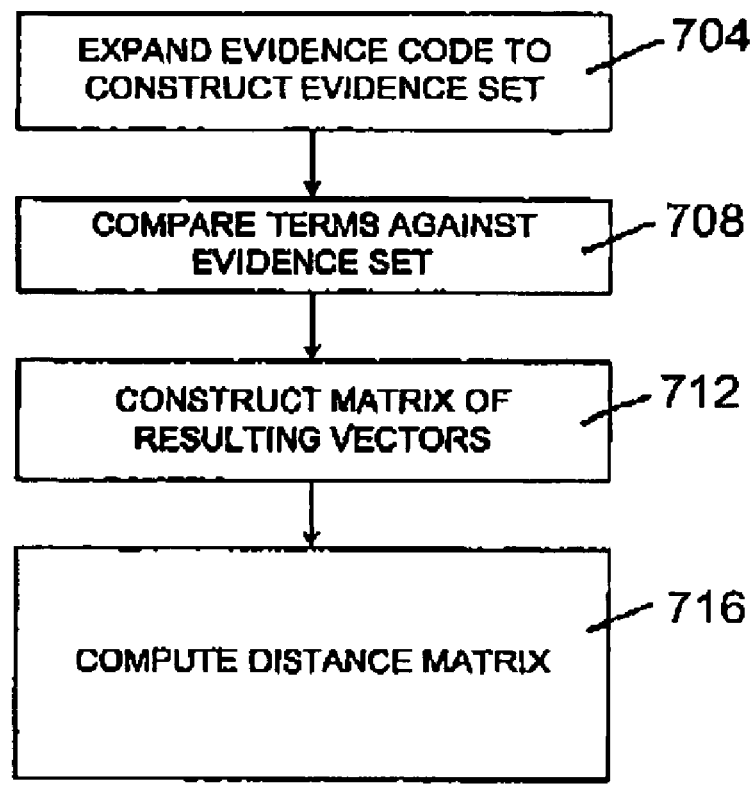
FIG. 7 illustrates a flowchart of processing according to the invention, in one regard.
FIG. 8 illustrates an example of a matrix of relevance scores, according to an embodiment of the invention.

According to a flowchart illustrated in FIG. 7, a process for constructing a distance matrix between ontology terms measured against a specific document set (e.g., a set of documents containing similar information, scientific papers, patents literature, project notes, etc.) may include one or more operations.

In an operation 704, an evidence code may be expanded to construct a evidence set. An evidence code may comprise a pointer to a database entry, document, or document set that contains concepts that describe an ontology term. An evidence set may include, in some embodiments, sets of documents chosen because they contain a high density of concepts that are relevant to a specific ontology term.

According to an embodiment of the invention, the system may use an evidence code supplied in the ontology term definition. A document or database entry supplied by the evidence code can be expanded in a number of ways including, for example, using a navigation function to the most closely-related document or database entity set. An entity may, according to an embodiment, include a uniquely-defined entry in a database table.

Navigation may include the process of identifying related entries in other database tables that may be relevant to a given entity. This expansion may increase the number of documents in an evidence set associated with an ontology term from 1 to a larger (e.g., predetermined) number. This increased set size may allow a categorization engine to better discriminate concepts and distinguish between closely-related ontology terms.

In an operation 708, the system may compare each of the ontology terms against the constructed evidence set by using a semantic analysis engine (e.g., a Probabilistic Latent Semantic Analysis engine).

According to one embodiment, the comparison of ontology terms against the evidence set may be performed by seeding a categorizer (e.g., categorization engine) with ontology terms, and comparing each of the evidence sets against part or all of the set of ontology terms.

According to one aspect of the invention, the system may use the Probabilistic Latent Semantic Analysis (PLSA) engine. This engine may employ a plurality of algorithms to run both indexing of concepts in a document, and categorization of the content of a document. During indexing, the engine may identify the hidden (latent) pattern of co-association of tokens in a set of documents, and create an inverted index of the positions of the resulting concepts so that they can be rapidly identified during a later search. Categorization (or classification) may aim to create a consistent structure for a set of documents, mapping the content of the documents into a series of topic categories.

In an operation 712, a matrix of resulting vectors (e.g., words and relevance score pairs) may be constructed. A distance matrix may, in an operation 716, be computed (e.g., based on a pairwise dot product of the vectors of the matrix).

According to an embodiment of the invention, the system may establish a reference point for evaluating the distance between any pair of ontology terms in a given document space based on plurality of user-enabled pre-requisites. In some embodiments, a definitive source of all known information may be required as the standard against which the concepts may be judged. The system may establish the relevance of a given concept against the document set. In some embodiments, the system may further cluster the concepts' relevance scores to remove under and over responders and synonyms.

According to an embodiment of the invention, the first stage in evaluating a term-document set relevance score may be to decide on an ontology (e.g., GO) and a target document set (e.g., Medline abstracts). According to one embodiment of the invention, the system may enable a user to provide the evidence code and external references which may allow a set of documents and database entries to be gathered that are highly relevant to the ontology term. According to one embodiment of the invention, the evidence set may include a much wider set of textual descriptions of functionality (e.g., expression, regulation and disease association) than the simple ontology term description, and may therefore be more discriminating.

According to an embodiment of the invention, the system may extract statistics measuring the relevance of a term to a document set. This may be used to generate a matrix of relevance scores, as illustrated in FIG. 8, by comparing each of a plurality of ontology terms against the evidence set for each of the plurality of ontology terms.

According to one embodiment, within this matrix, any terms that score consistently high against all documents (e.g., "Induction") may show very limited discrimination and could be removed. This may be done with a consideration of the overall information content of a given ontology term in the context of a document.

Highly specific words like "Opsin," for example, may be described as having a high information content, whereas more frequently occurring words, like "Cell," may be described as having a low information content. High information content words may be more likely to be discriminating than low information content words. In some embodiments, this information content factor may be normalized to avoid invalid comparisons. Any terms that score consistently low (e.g., "Signal") may show limited relevance and may be removed. In other embodiments, if the profile of scores for any two terms appears to be very similar, it may likely be that these terms are so highly related that they may be considered synonyms, and may be removed.

According to an embodiment of the invention, once a number of terms in the matrix has been reduced, a matching exercise of distance matrix analysis may be run again with the reduced starting ontology. This time, term vectors (which may describe the weighted list of words associated with a term) may be retrieved. In some embodiments, term vectors may contain mathematical descriptions of concepts. These term vectors may then be compared pairwise using a dot product function to establish a set of pairwise term-term distances in a distance matrix. This distance matrix, which may be specific to the ontology and document set (or evidence set) used, may include quantitative information on the similarity or dissimilarity of any two concepts derived from a specific ontology in the context of a specific document set.

According to another embodiment of the invention, multiple distance matrices may be created for different document sets, and may be quite flexible. For example, a distance matrix derived from GO and Medline may allow a user to identify genes being co-reported as being involved in specific disease mechanisms.

Figure 9:
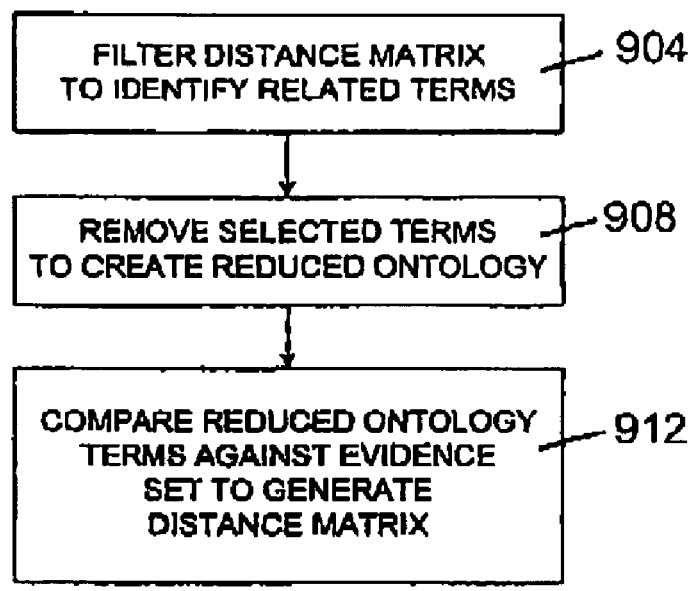
FIG. 9 illustrates a flowchart of processing according to the invention, in one regard.

FIG. 9 is a flowchart illustrating the process of filtering a discriminable set of ontology terms against a specific document set using a distance matrix, according to the invention in one regard.

In an operation 904, the system may filter the distance matrix specific to the ontology and document set to identify identical or closely-related terms (e.g., synonyms or other relationships), according to a predetermined discrimination criteria.

In an operation 908, the system may remove selected terms (e.g., synonymous terms) from the ontology to create a reduced ontology, and in an operation 912, may compare some or each of the terms in the reduced ontology against the evidence set (e.g., using a semantic analysis engine) to generate a resulting distance matrix for the given validated ontology against the specified document set.

One advantage of this methodology is that, unlike prior "un-rooted" trees where relationships could only be inferred through the ontological hierarchy, this approach enables the ontology and distance measures to be quantified and visualized using a hierarchical map displayed with a rooted tree.

Figure 10:
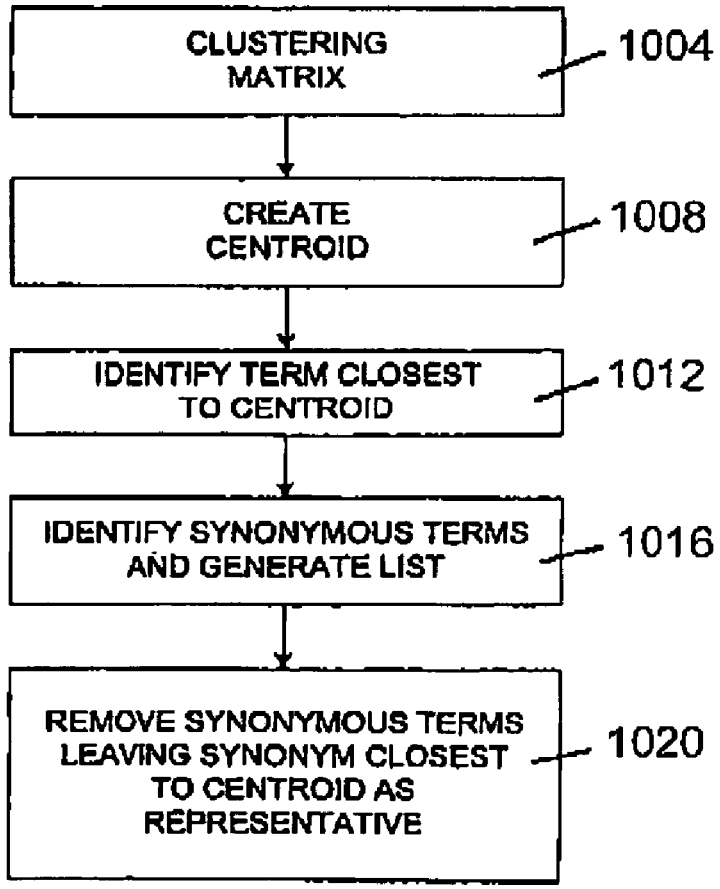
FIG. 10 illustrates a flowchart of processing according to the invention, in one regard.

FIG. 10 is an illustration of additional operations that may be involved in the operation 904 (FIG. 9) of filtering the distance matrix, according to an embodiment of the invention. In an operation 1004, the system may analyze and cluster the matrix (e.g., using a discrete cosine transformation) to reduce the ontology term space. In an operation 1008, the system may create a cluster centroid for each set of synonymous terms. In an operation 1012, the system may identify the ontology term closest to the centroid. In an operation 1016, the system may further identify synonymous ontology terms and generate a synonym list for the ontology and document set. In an operation 1020, the system may further remove synonymous terms from the ontology leaving the synonym closest to the cluster centroid as a representative of the cluster.

Figure 11:
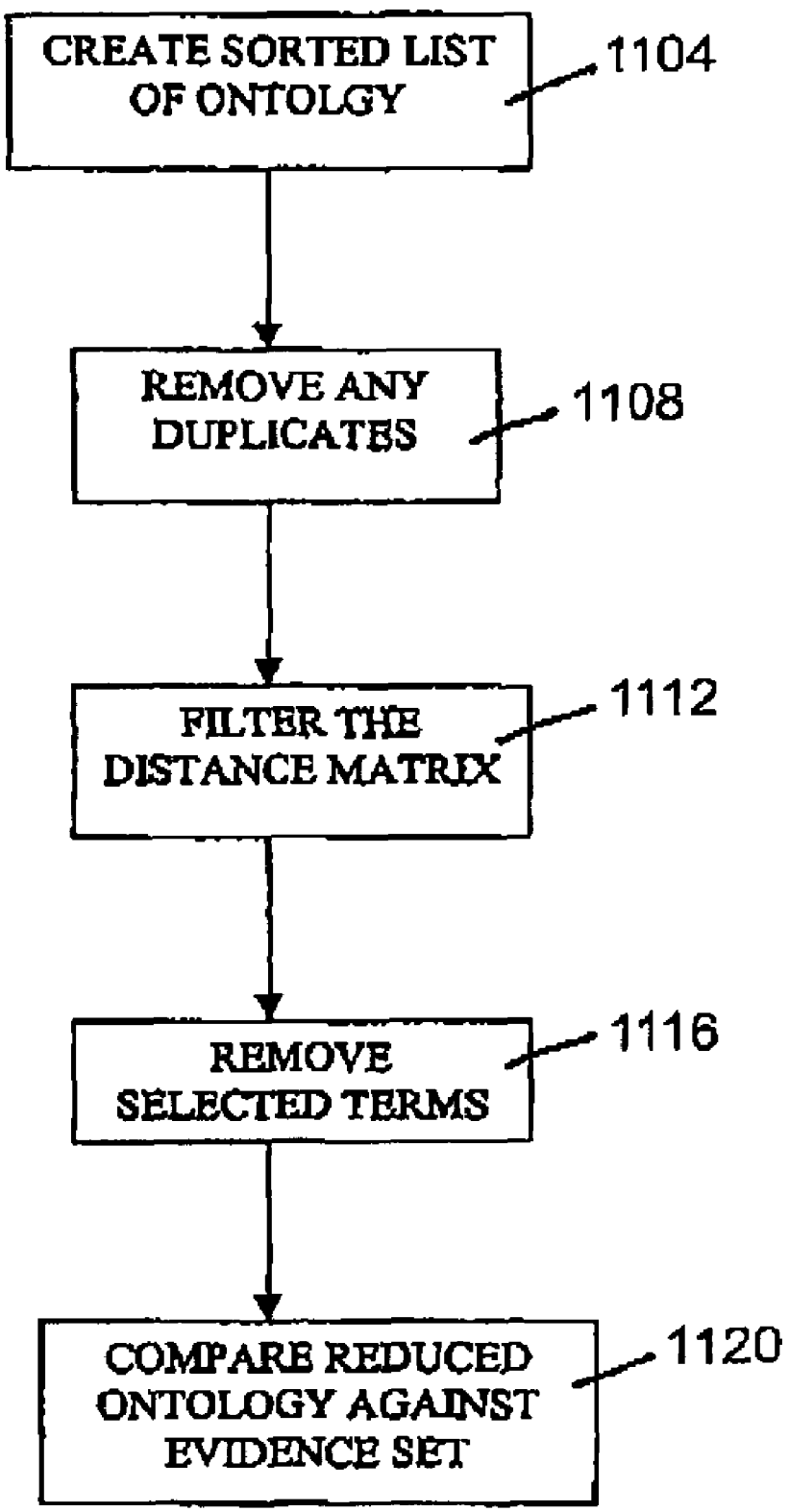
FIG. 11 illustrates a flowchart of processing according to the invention, in one regard.

According to an embodiment of the invention, illustrated in FIG. 11, multiple ontologies may be combined into a single aggregate ontology validated against a specific document set using the distance matrix.

In an operation 1104, the system may create a sorted list of ontology terms from all of the ontologies that are to be combined. In an operation 1108, the system may remove any duplicates from the list and, in an operation 1112, the system may filter the distance matrix specific to the ontology and document set to identify identical or closely-related terms (e.g., synonyms or other relationships) according to a predetermined discrimination criteria.

In an operation 1116, the system may remove selected terms (e.g., synonymous terms) from the ontology to create a reduced ontology. In an operation 1120, the system may compare some or each of the terms in the reduced ontology against the document set (e.g., using a semantic analysis engine) to generate a resulting distance matrix for the given validated ontology against the specified document set.

According to one aspect of the invention, various different ontologies available in a domain may be combined to create an aggregate ontology, which may then be validated as described above. In the life science domain, this may be useful as there exist several different ontologies with different foci. For example, in the life sciences domain, GO has a genotypic focus, whereas UMLS is clinically and phenotypically oriented. The specific Enzyme Classification scheme has a very narrow focus on enzymatic function and processes. The system of the invention may combine these to create an aggregate ontology.

According to another aspect of the invention, the system may enable a user to create a combined word list for ontology terms from the various semantically-poor source ontologies. The system may create empirical distance matrices between terms. In some embodiments, the system may reconcile semantic representational differences that might exist between these source ontologies.

According to one aspect of the invention, the system is capable of establishing a term relevance distance score. For example, analysis of a set of documents including the token "Computer" has shown highly-related tokens such as "Mouse," "Keyboard," and "Monitor." A lesser, yet still significant relationship has been shown to the tokens "Network," and "Cluster." This pattern of relationships, between these tokens, may define a concept of a computer in the set of documents used to train the system. The last distinction may be important, as the relationships and relevancies may change with different document sets.

For example, while "Mouse" may be highly relevant to "Computer" in this document set, it may be more relevant to "Transgenics," "Rat," and "Knock-outs" in a pharmaceutical target validation document set. In information retrieval, this ability to differentiate between the context of a document and the topics to which it refers, is known as categorization or classification. The system of the invention may provide components for categorization and classification, and may establish a term relevance distance score.

According to another embodiment of the invention, a comparison step may be performed by seeding a categorizer with a reduced set of ontology terms, comparing each of the evidence sets for the reduced set of ontology terms against the reduced set of ontology terms, and constructing a matrix of the resulting relevance scores. The resulting matrix may form the distance matrix for the given validated ontology against the specified document set. By using a different document set during the categorization, distance matrices for different information spaces can be created.

According to one embodiment, the system may categorize ontologies. For example, the system may enable a user to select one or more categories of ontologies. In another embodiment, the system may identify one or more categories of ontologies based on user's profile information and return the results of the search relevant to the user's profile.

According to another embodiment, the system may provide an optimized version of a latent semantic analysis technique, also employing Expectation Maximization as a mechanism of improving its categorizer and indexer training. This may be best suited to large, complex unstructured datasets, particularly where a domain taxonomy or ontology exists. According to another embodiment, domain taxonomy or ontology may be used to seed categorizations and determine the specific relevance of an article to a given type of user.

In one aspect of the invention, when the categorizer is run with a seed ontology, documents may be placed into a predetermined set of bins established by the curator of the data sources. This is known as supervised learning. In another aspect of the invention, when no seed may be provided, the system may discover its own concepts and categories in an unsupervised manner. In the latter case, the system may continually evaluate the performance of the categories it discovers and evaluate how well they represent the content and topics of data that have been categorized.

If, for example, the system creates too many categories, then the data may be overfitted, and the categories may become too narrow and specific, and the abstract properties and relationships embodied in the categories may become no more informative than a concept index. If the categories are too broad, by contrast, topics may begin to blur into one another, and the system may lose the subtlety needed to represent the relationships between sub-categories.

According to one embodiment of the invention, the system may maintain this balance of abstraction versus specificity in both supervised and unsupervised learning categorization.

Another aspect of the invention relates to augmenting an existing ontology against a specified document set. According to one embodiment, the system may automatically identify concepts present outside an ontology space using unsupervised categorization. In an unsupervised mode, the categorizer may examine all of the data in a document set and may attempt to identify all the concepts within it. These concepts may form the basis of the ontology terms.

According to an embodiment, a codified knowledge contained in existing validated ontologies for a domain should be considered. Otherwise, an ontology system may discover new concepts inside the ontology space which, although valid from an information retrieval (IR) perspective, may nonetheless be confusing or unrecognizable to a user (e.g., a biologist). To avoid ignoring this information, the system of the invention may combine the results of the unsupervised categorization with the list of validated ontology terms, and then validate the resulting combined ontology. By clustering the resulting relevance matrix around the preexisting validated ontology terms, the system may ensure that this acts as a consistent seed to knowledge discovery, and does not get lost in the process.

Figure 12:
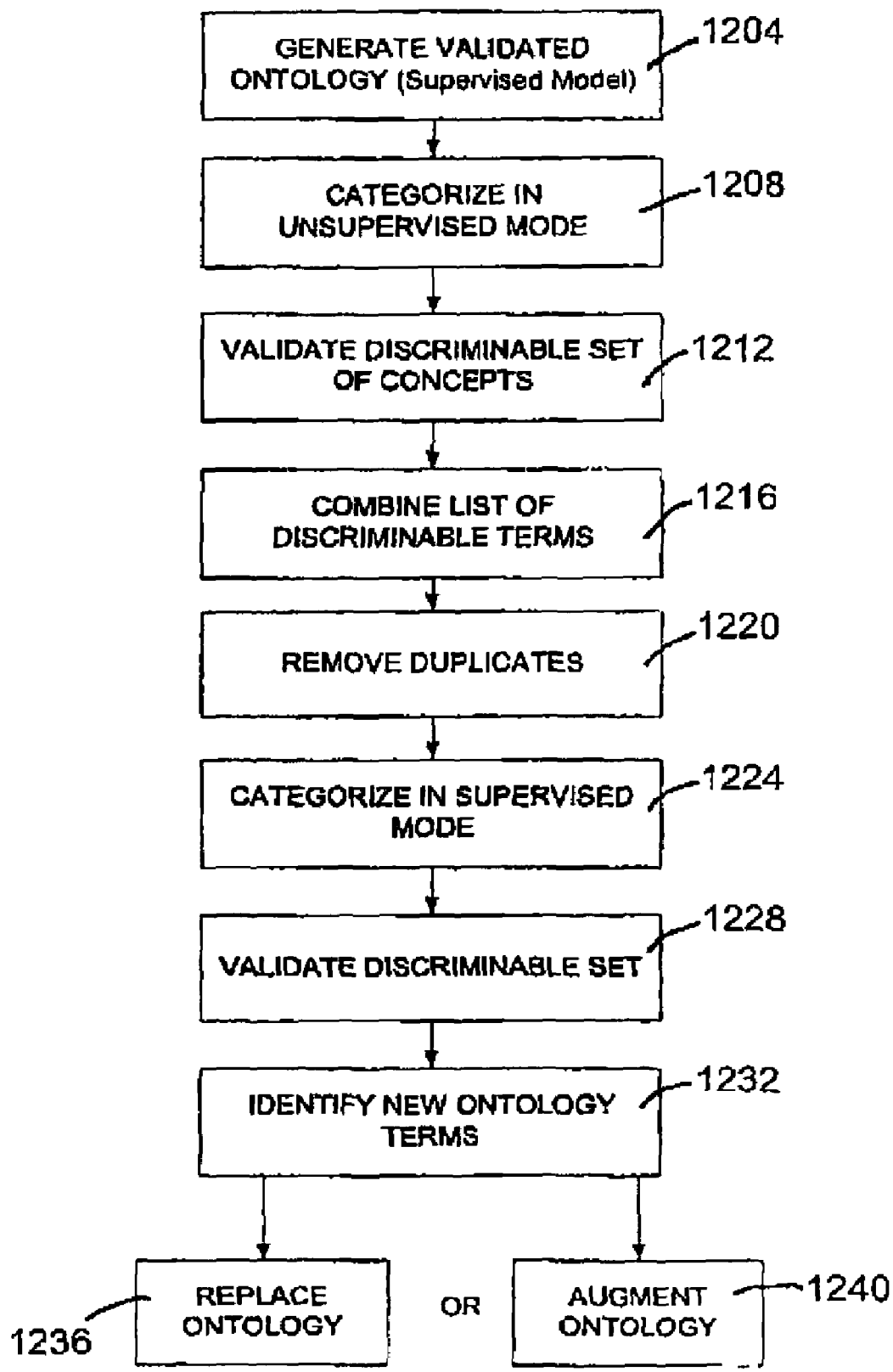
FIG. 12 illustrates a flowchart of processing according to the invention, in one regard.

According to an embodiment of the invention illustrated in FIG. 12, augmentation may be achieved in a number of operations. In an operation 1204, the system may generate a validated ontology against a specific document set. This operation 1204 may be referred to as running in supervised mode, wherein running in supervised mode may include running the categorizer with a seed ontology to force the categorizer to identify only concepts matching the supplied list of terms.

In an operation 1208, the system may re-run the categorizer in an unsupervised mode without providing a seed ontology. The unsupervised mode may include running the categorizer without any a priori knowledge or structure to identify any concepts that may be statistically significant from an information content perspective in the specified document set.

In an operation 1212, the system may validate a discriminable set of concepts from the unsupervised categorization using the methodology described above. In an operation 1216, the system may combine the lists of discriminable terms from the validated ontology (supervised categorization) and validate concepts (unsupervised categorization). In some embodiments, the discriminable terms may be based on the term being differentiated statistically above a defined threshold in a distance matrix.

In an operation 1220, the system may remove duplicate terms and, in an operation 1224, run the categorizer in a supervised mode using the combined term list as a seed ontology. In an operation 1228, the system may also validate the discriminable set of combined ontology terms using the methodology described above. The system may, in an operation 1232, identify new ontology terms not contained in the original existing ontology. In some embodiments, as shown in an operation 1236, the system may perform refinement of the existing ontology by replacing the original ontology with the new validated combined ontology. In other embodiments, as shown in an operation 1240, the system may perform automatic discovery of new ontology terms for augmentation of an existing ontology, by selectively adding any newly discovered terms (that may be unique to the new validated combined ontology) to the list of ontology terms in the existing ontology.

Figure 13:
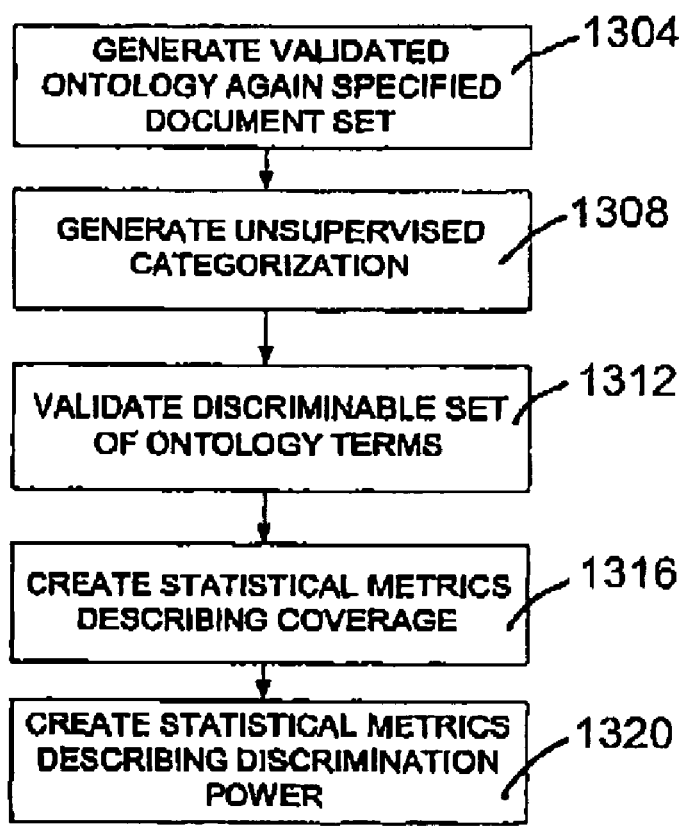
FIG. 13 illustrates a flowchart of processing according to the invention, in one regard.

According to an embodiment of the invention illustrated in FIG. 13, the scope of an ontology may be validated against a specified document set. According to one embodiment of the invention, this validation may be achieved in a plurality of operations including generating a validated ontology against a specific document set (operation 1304), generating an unsupervised categorization of the specific document set (operation 1308), validating a discriminable set of combined ontology terms (operation 1312), creating statistical metrics that describe the coverage of the validated ontology terms versus the combined ontology terms (operation 1316), and creating statistical metrics describing the discrimination power of the validated ontology terms versus the combined ontology terms (operation 1320).

As recited above with reference to FIG. 1, ontology system 100, semantic mapper 104, semantic map module 108, concept-based query module 112, structured query module 116, unstructured query module 120, prioritization module 124, and portfolio management module 128 may all comprise an application. The application may be a stand-alone software application run on a workstation. The application may also be incorporated into an existing software application, or according to an alternative embodiment, a server may host the application, thus requiring a user at a workstation to access the server over a network to use the application.

FIGS. 14–24, described in detail below, are each examples of views that may be presented to a user working with the application. It should be understood that the views are exemplary and may differ in appearance, content, and configuration. Further, and as may be described herein, the terms "button," "pull-down menu," "tab," "click-box," "check-box," "hypertext link," and "hot link," are each particular examples of a generic "selection portion" which may comprise any known navigational tool that enables users to select, access, display, or navigate through the various views, portions, or modules of the application. The selection portions may be accessed using any known input device associated with a workstation such as, for example, a keyboard, computer mouse, light stylus instrument, or finger or other body part in a touch-screen implementation.

While a selection portion may be described and illustrated as a button in one embodiment, it could comprise a different selection portion (e.g., a check-box) in an alternative embodiment. These selection portions may be present in addition to the various navigational tools that may be unique to, or associated with, a web browser (e.g., Netscape™) or other Graphical User Interface (GUI) that may be used to access the application in certain embodiments.

Figure 14:
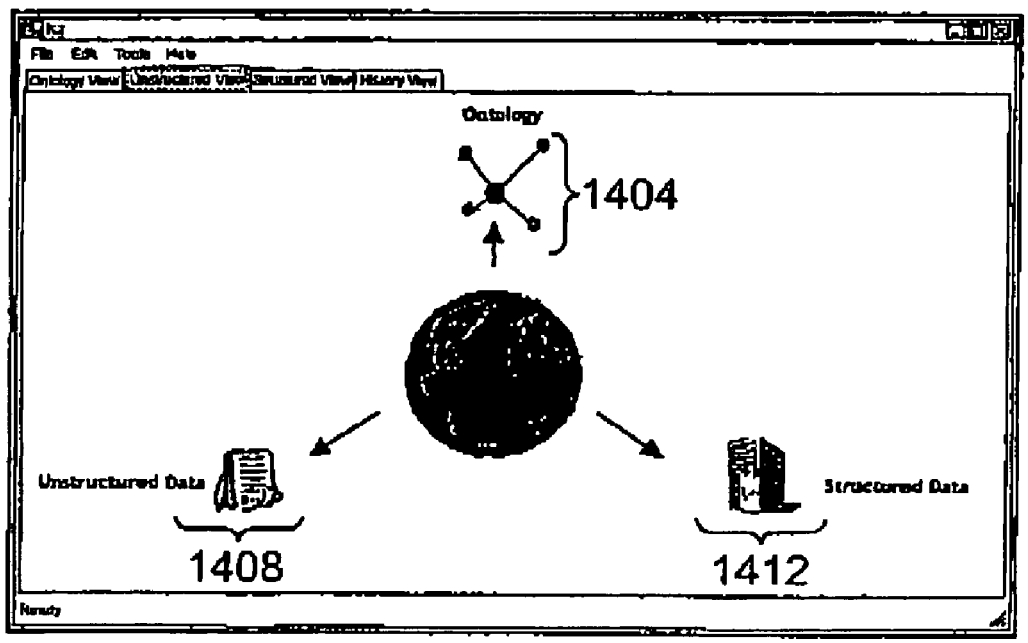
FIG. 14 illustrates an example of a view that may be presented to a user, according to an embodiment of the invention.

FIG. 14 is an example of a welcome view 1400 that may presented to a user when the application is first accessed. From this view, ontology, unstructured, and structured data perspectives (or views) may be accessed by selecting or "clicking-on" icons 1404, 1408, and 1412, respectively. According to one embodiment, a login dialogue may be presented to a user if the application is operating in a secure mode.

Selecting one of the icons (1404, 1408, 1412) may initiate a new user session. The start of a new user session may also begin a new recording of session events in an application history (described in detail below). The following views illustrate how a user session might proceed.

A user may, for example, select icon 1404 to access an ontology perspective. According to an embodiment of the invention, the application may include two representations of a loaded ontology. The first representation may comprise the ontology as it is originally loaded into the application. The second representation may comprise a processed perspective that the application uses to provide semantic compression and distance mapping of original ontology terms.

Figure 15:
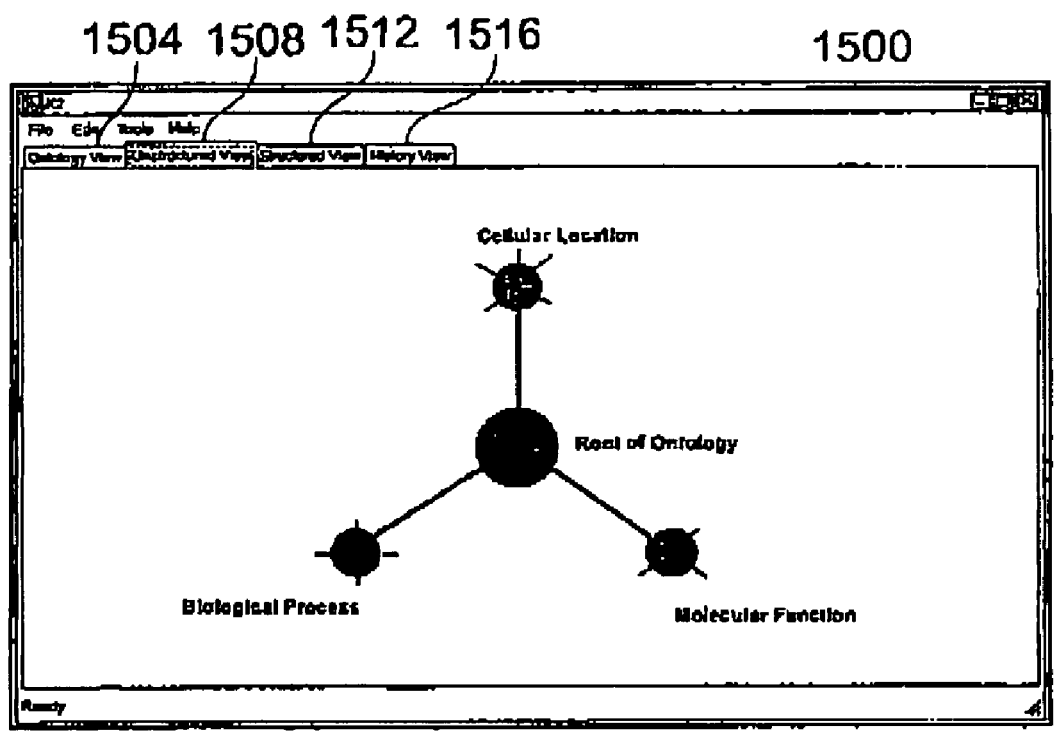
FIG. 15 illustrates an example of an ontology view (or perspective), according to an embodiment of the invention.

According to an embodiment of the invention, a user may familiarize himself with an ontology by entering an ontology composition perspective, illustrated as view 1500 in FIG. 15. This view may allow a default unprocessed ontology to be navigated. Upon entering view 1500 from welcome view 1400, a user may be presented with a stick and ball view of the ontology starting at the ontology root node. All terms directly descending from the root node may be shown radiating out from the root with equidistant distribution. View 1500 may further comprise a "ontology view" tab 1504, "unstructured view" tab 1508, "structured view" tab 1512, and "history view" tab 1516 for enabling further navigation through the various views of the application.

Figure 16:
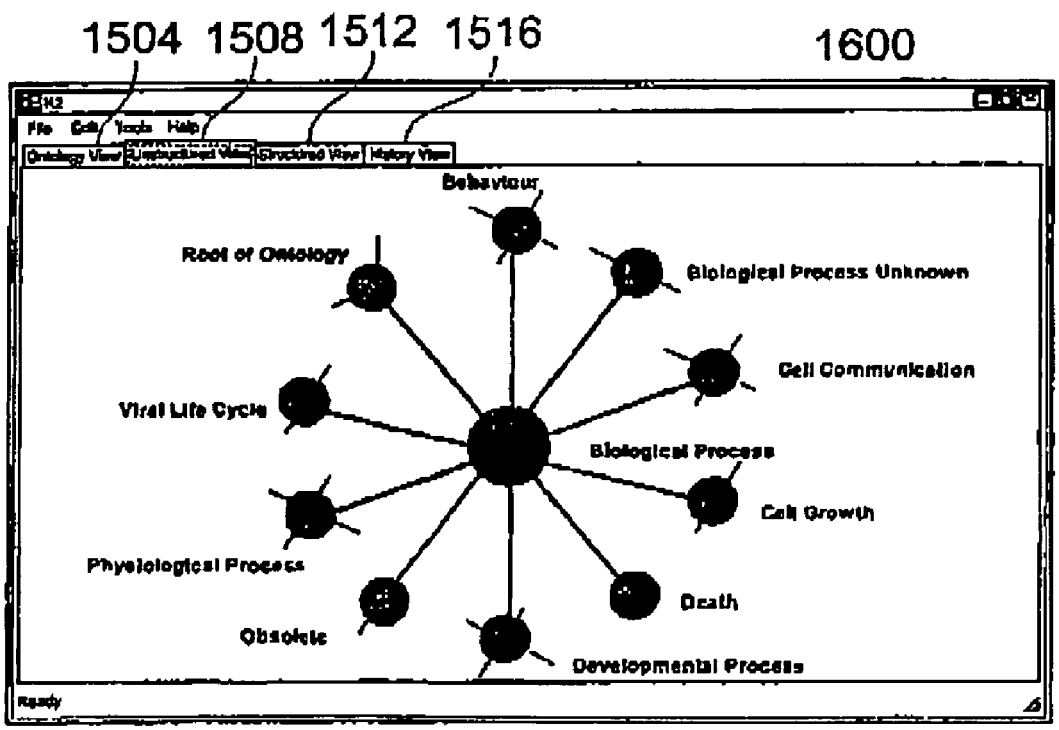
FIG. 16 illustrates an example of an ontology view (or perspective), according to an embodiment of the invention.

According to an embodiment of the invention, an ontology may be deliberately limited to showing only immediate descendants of a main node in focus. This may be done to reduce the complexity of the graphics presented to the user. Short lines that extend from each of the first-level derivatives may represent second-level derivatives. The number of short lines may indicate the number of available navigable paths from that derivative. View 1500 illustrates this using the root node of the Gene Ontology. For example, a user may navigate through the ontology by clicking on one of the first-level derivatives of the term in focus. If a user felt that the Biological Process term was of interest, for interest, clicking this term may move the term to the center of the view. The Biological Process term derivatives may then animate and expand to occupy a full view with their derivatives again represented by short lines. An example of a resulting screen is illustrated in FIG. 16, as view 1600.

According to an embodiment of the invention, it may be possible to initiate a search from any view of the application. The search context may be based on the perspective and the view from within which the search is initiated. According to an embodiment, a user may start a search simply by typing. The act of typing may automatically cause a search dialogue (not illustrated) to open within a current view. Text entered by the user may automatically be placed into the search dialogue.

Figure 17A:
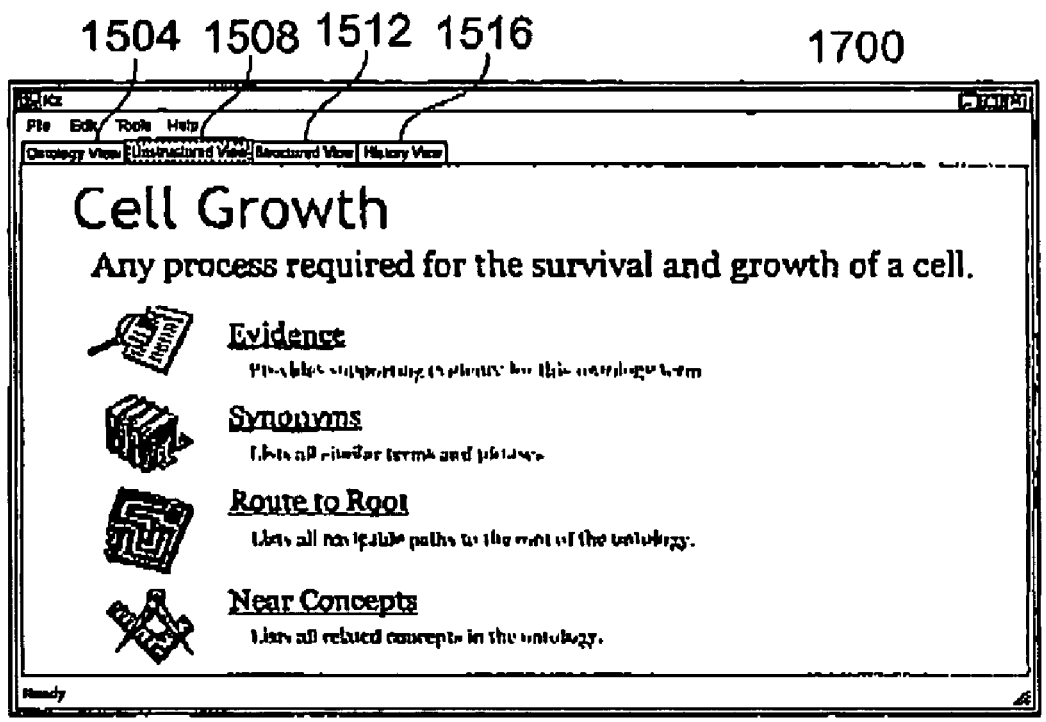
FIGS. 17A–17B illustrate examples of ontology properties views, according to an embodiment of the invention.

Within an ontology composition view (e.g., view 1600), a search may allow a user to find and navigate directly to an ontology term. Once a user has navigated through the ontology to a term of interest, the properties associated with that term may be viewed by selecting the term (e.g., by "right-clicking" on the term). This may take the user to an ontology Properties view. For instance, in view 1600, if a user were to select the "cell growth" term, he or she may be presented with view 1700 as illustrated in FIG. 17a.

Figure 17B:
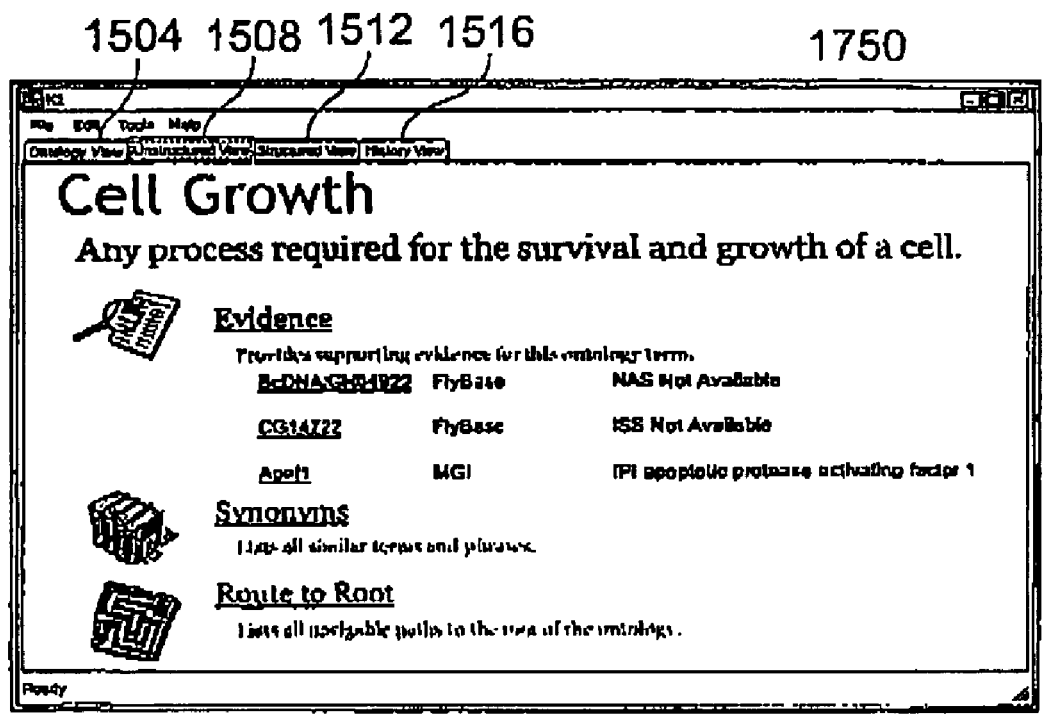

According to an embodiment, a properties view (e.g., view 1700) may display the name and description of the term selected, together with an overview of all properties associated with that term. A 'Route to Root' entry may be made available to a user, displaying all available paths back to the ontology root via all intermediate terms. Clicking on a property name or its associated icon may expand each available property. An expanded view 1750, as illustrated in FIG. 17b, may display the full detail of the property.

Figure 18A:
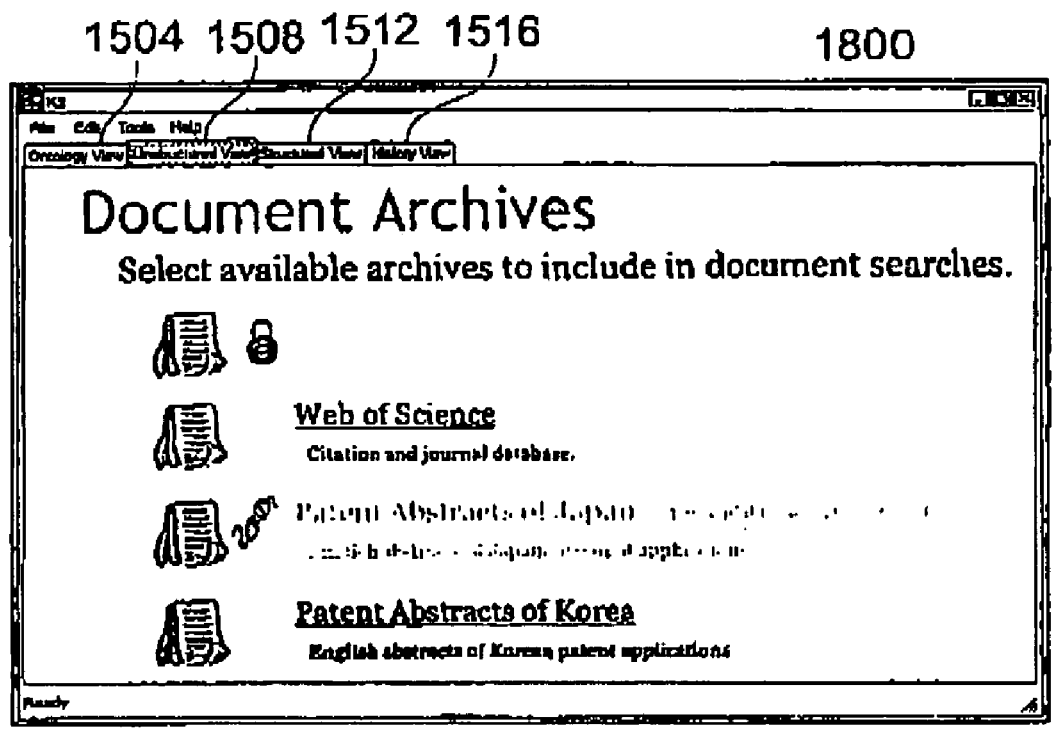
FIGS. 18A–18B illustrate examples of document searching views, according to an embodiment of the invention.
Figure 18B:
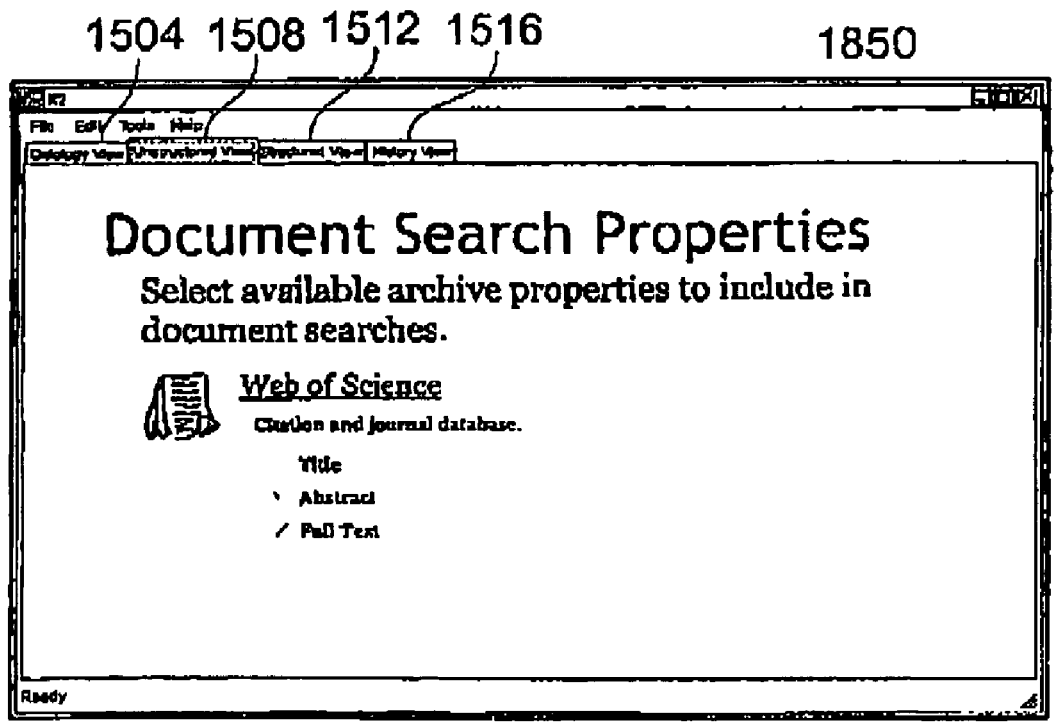

According to an embodiment of the invention, document searching may be available from within an unstructured perspective. This perspective may be accessed from welcome view 1400 by selecting icon 1408, or by selecting "unstructured view" tab 1508 from any other view. The first view of the unstructured perspective may comprise the Document Archives view 1800, as illustrated in FIG. 18a.

View 1800 may display all document archives defined within the application. View 1800 may enable a user to select those archives from which documents should be retrieved. View 1800 may also include an indication (e.g., text message) should any archive be unavailable for searching. According to an embodiment, "right-clicking" or otherwise selecting an archive (e.g., "Web of Science") may cause an expanded "in-page" menu to appear, such as that illustrated in view 1850 in FIG. 18b. Selecting a properties menu item from this menu may display the properties for all of the selected document archives.

According to an embodiment of the invention, the properties for each archive may display or otherwise indicate which parts or sections of a document (e.g., title, abstract, full-text) have been indexed, and are therefore searchable. As a default setting, all of the fields may be marked as selected, and a search would thus include all of these fields. A user may, according to one implementation, de-select selected fields. Any field that is de-selected may then be excluded from subsequent document searches regardless of how further document searches are initiated. To re-select excluded document fields, a user may return to this view and re-select the deselected field that is to be included.

Figure 19A:
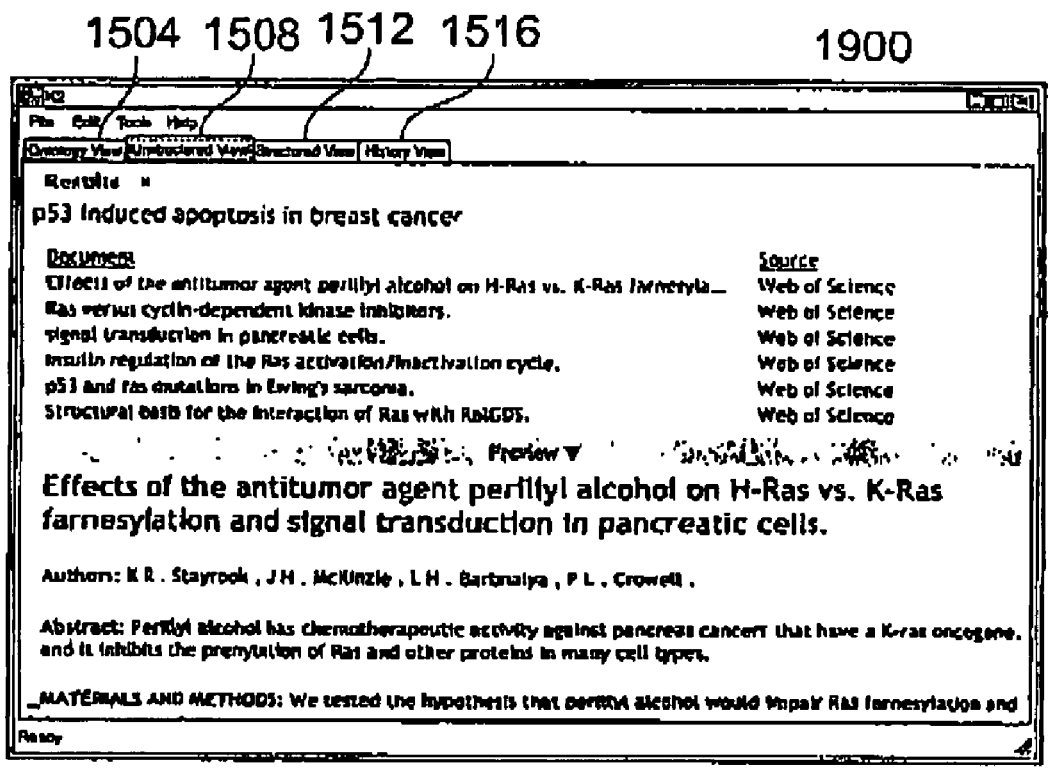
FIGS. 19A–19B illustrate examples of search results views, according to an embodiment of the invention.
Figure 19B:
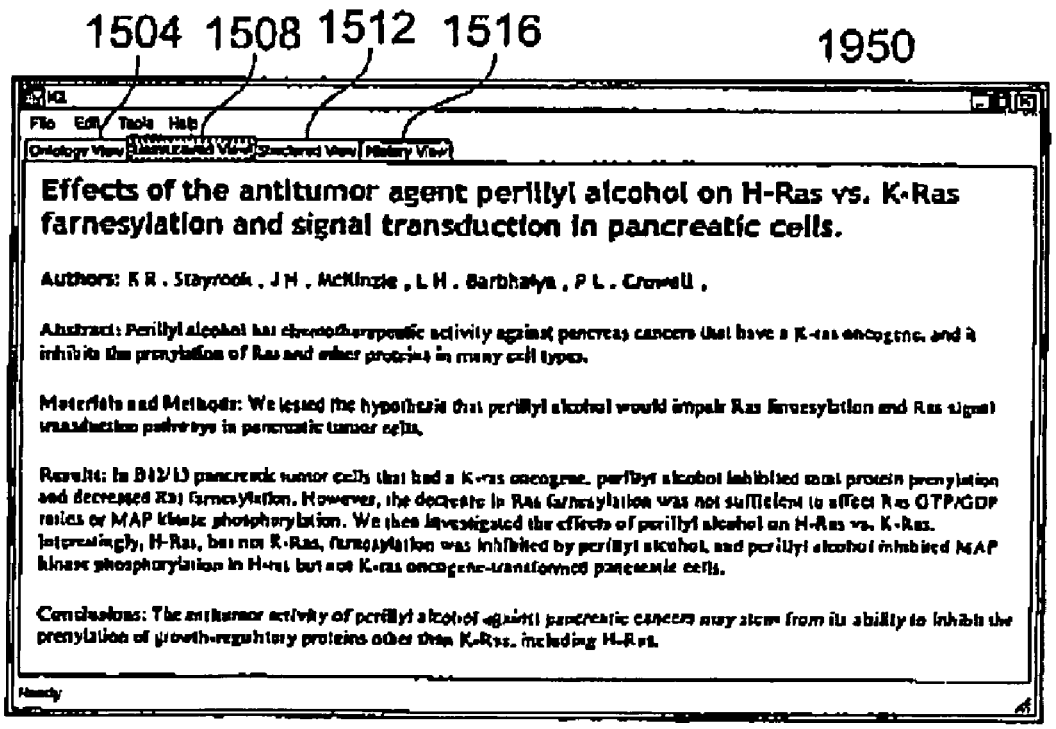
Figure 20:
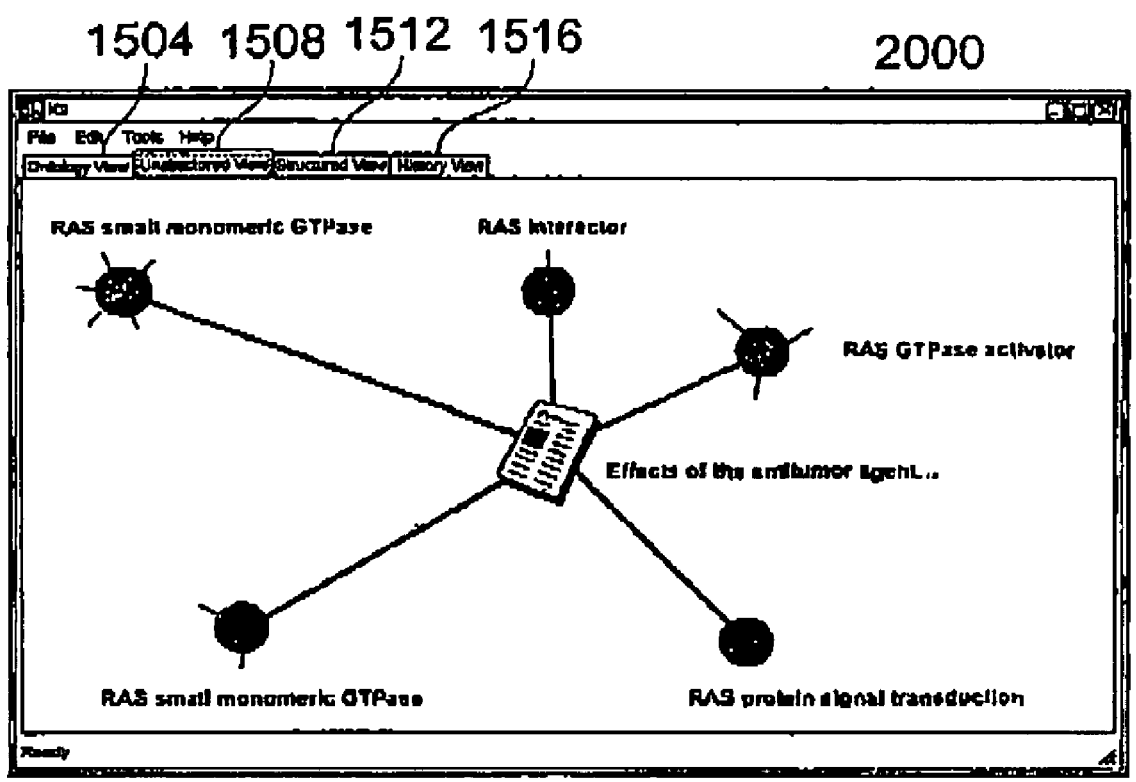
FIG. 20 illustrates an example of an ontology view (or perspective), according to an embodiment of the invention.

In the same manner in a which a search may be undertaken from within an ontology perspective as described above, a user may initiate a document search by inputting a query in any of the unstructured perspective views. The action of typing may cause a search dialogue window to appear within a current view. Once a search is submitted, documents matching the query and/or meeting document archive constraints may be returned into an unstructured perspective workspace view 1900, as shown in FIG. 19a. A workspace may also enable all results to be previewed. As shown in view 1950 of FIG. 19b, any result may be viewed within it's own results pane by selecting (e.g., "double-clicking") the result row.

According to an embodiment of the invention, a user may view ontology concepts relevant to a particular document (by changing to an ontology perspective) by selecting "ontology view" tab 1504. As shown in view 2000 in FIG. 20, an icon representing the result may be centered in an ontology workspace. Each of the concepts relevant to the document may be arranged around the document with the distance from the document representing how relevant the concept is to the document.

Database searching may be enabled from within a Structured perspective. This functionality may be accessed from welcome view 1400 (FIG. 14) by selecting the Structured Data icon 1412, as well as by selecting the "Structured View" tab 1512 from any other perspective (or view).

Figure 21A:
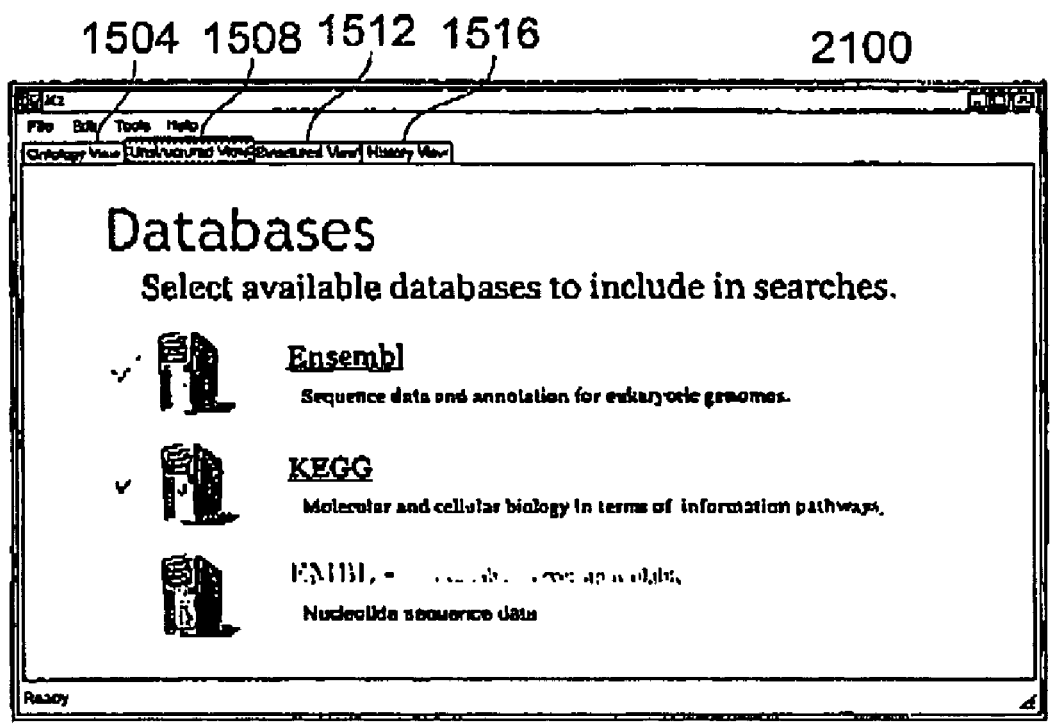
FIGS. 21A–21C illustrate examples of structured database views, according to an embodiment of the invention.
Figure 21B:
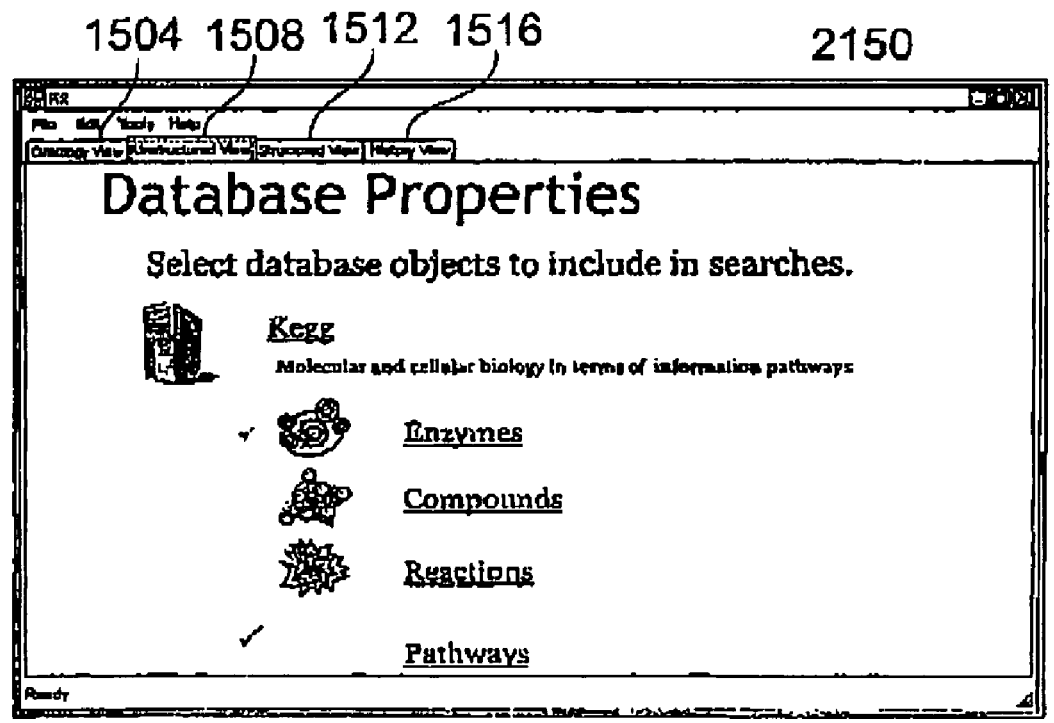

According to an embodiment of the invention, a first of many Structured views presented to a user may be database view 2100, as shown in FIG. 21. Database view may display all databases defined within the application. Database view 2100 may enable a user to select those databases from which structured data can be retrieved. Should any database be unavailable for searching, this may be indicated on this view. According to an embodiment, "right-clicking" or otherwise selecting a database (e.g., "KEGG") may cause an expanded "in-page" menu to appear, such as that illustrated in view 2150 in FIG. 21b. Selecting a properties menu item from this menu may display the properties for all of the selected document archives.

According to an embodiment of the invention, the properties for each database may list which application domain objects are available from the selected databases. An application domain object is an object that may be configured into the application to represent a particular domain entity. The properties of these objects may also be configured as part of the application together with their mapping to individual database attributes. A database may contain multiple application domain object types, and a domain object may be mapped to multiple databases.

Figure 21C:
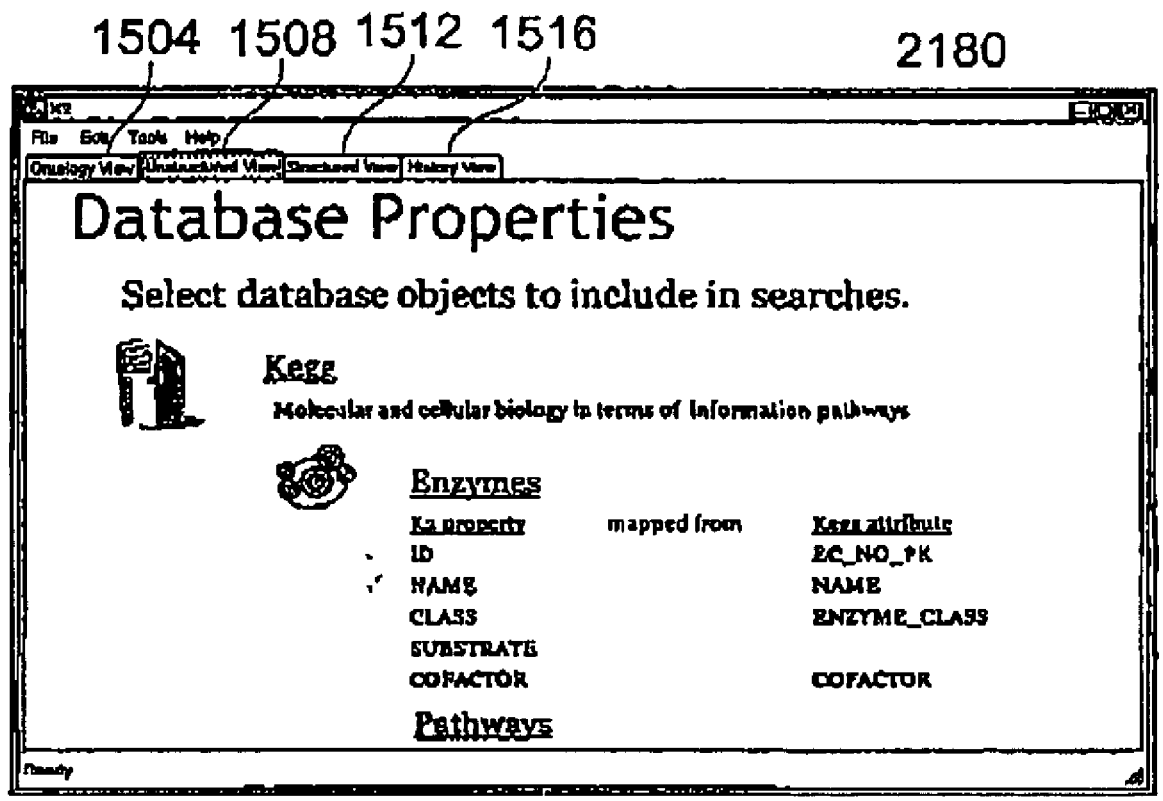

As illustrated in FIG. 21c, view 2180 may enable users to select and de-select various domain objects for each database. As a default setting, for each selected database, all of the domain objects may be marked as selected. Thus, a search would include all of these domain objects. Any object that is de-selected by a user may be excluded from all subsequent database searches regardless of how any further database searches are initiated. In order to re-include domain objects that are excluded, a user may return to view 2180 and re-select the de-selected object to be included. Database properties may be further expanded to show the properties of each application domain object. Each of the individual domain object properties may be selected or de-selected, further constraining any subsequent database searches. As with other queries, to initiate a search, a user may begin to type (or otherwise input) a query in any of the structured views. This action may cause a search dialogue to appear in a view that accepts user input.

According to an embodiment of the invention, structured queries may be based on application domain objects. This may enable a simple query language to be used. Once a query has been submitted, results matching the query and/or meeting the constraints may be presented in a structured workspace, such as view 2200 depicted in FIG. 22a. View 2200 may also enable all results to be previewed. Any result may further be viewed within its own results pane (or view) by selecting (e.g., "double-clicking") the result row.

According to an embodiment of the invention, selecting a result may enable a user to further search selected databases for other related application domain objects. Results from this search may be placed in a new result pane (or view).

Figure 22A:
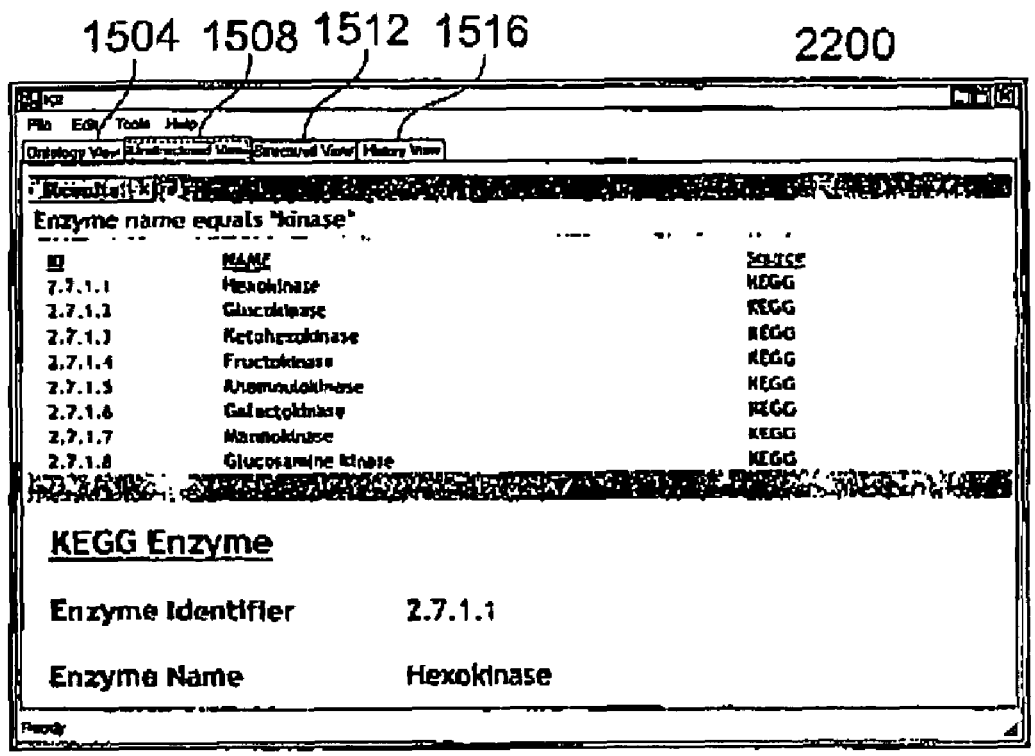
FIGS. 22A–22B illustrate examples of search results views, according to an embodiment of the invention.
Figure 22B:
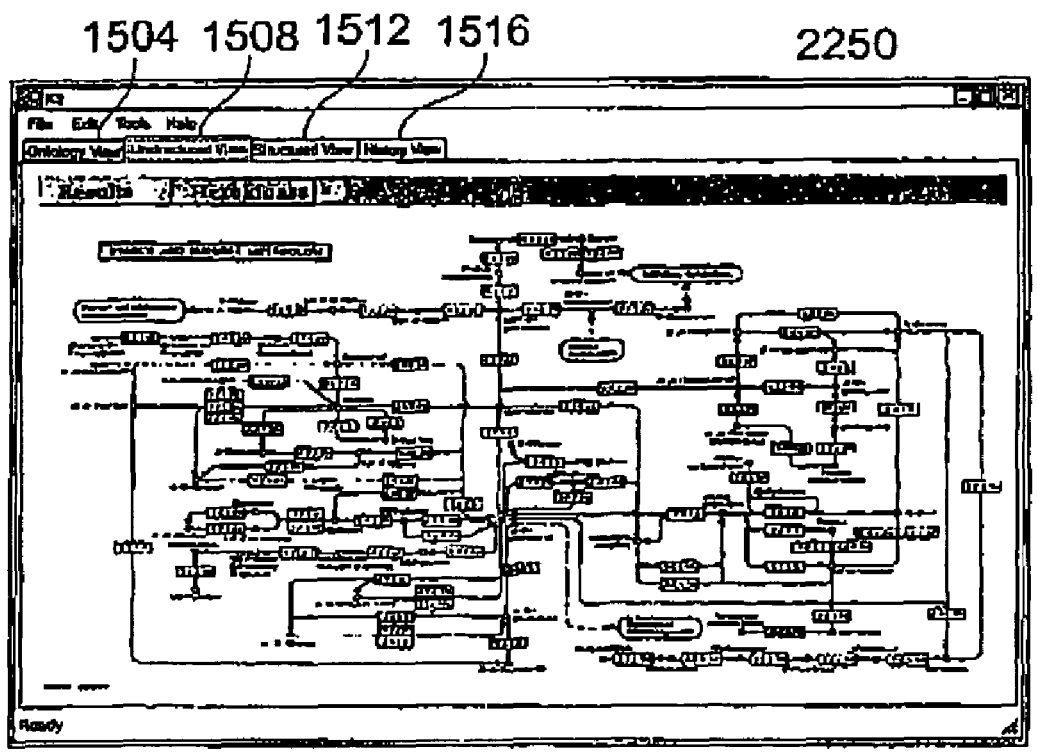
Figure 23:
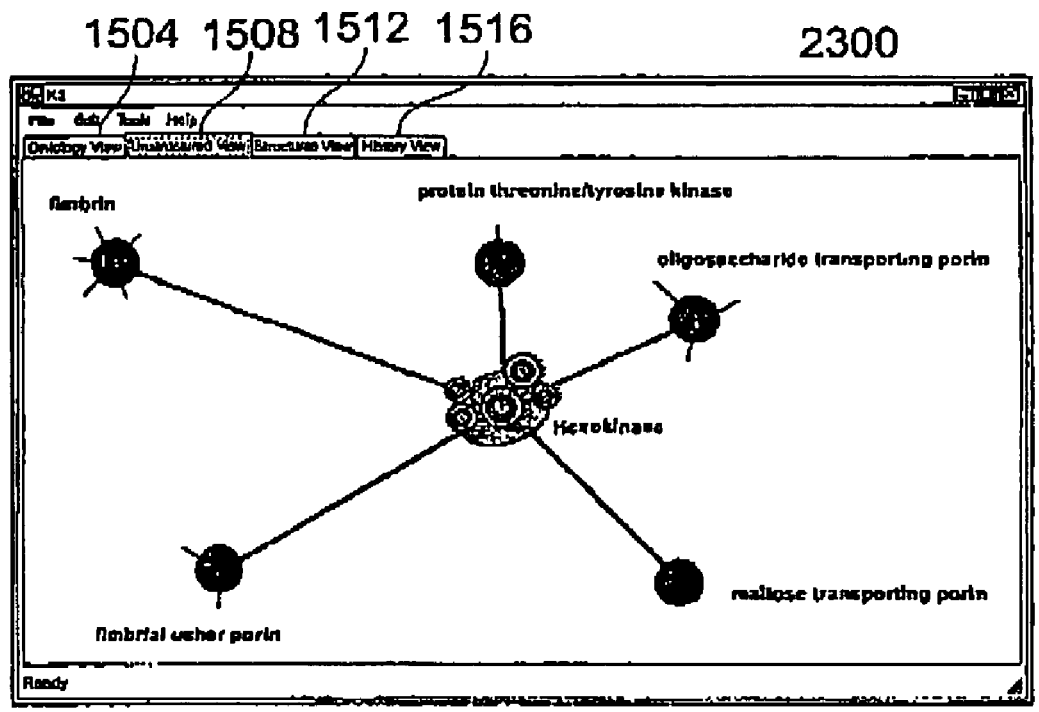
FIG. 23 illustrates an example of an ontology view (or perspective), according to an embodiment of the invention.

According to an embodiment of the invention, the application may accommodate multiple plug-able viewers. An alternate viewer for a particular data type may be selected, if available, through the use of a "right-click" "pop-up" menu or other user-accessible display available from within a results preview or individual results pane. View 2250, as illustrated in FIG. 22b, is an example of the use of a plug-able viewer for Pathways.

Switching to an ontology perspective from the structured perspective enables a user to view ontology concepts relevant to a particular application domain object. As shown in view 2300 of FIG. 23, an icon representing the selected row from the structured results may be centered in the ontology view 2300. Each of the concepts relevant to the application domain object may be arranged around the object, with the distance from the object representing how relevant the concept is to the object.

According to an embodiment of the invention, ontology linking functionality may be provided. From within an ontology view, a user may easily link to application domain objects or documents by using, for example, a "right-click" "pop-up" menu. This menu (not illustrated) may navigate a user to an ontology properties page, and also provide a list of available application domain objects. According to one embodiment, the list may be subjected to document archive and database constraints that may have been previously set.

Selecting an application domain object may cause all appropriate, selected databases to be searched for an application domain object type relevant to the selected ontology term. Results of the search may be displayed in the Structured data workspace. Selecting a 'Document' selection portion from this list may cause all selected document archives to be searched for the selected ontology concept. Results of the search may be displayed in the Unstructured data workspace (or view).

Figure 24:
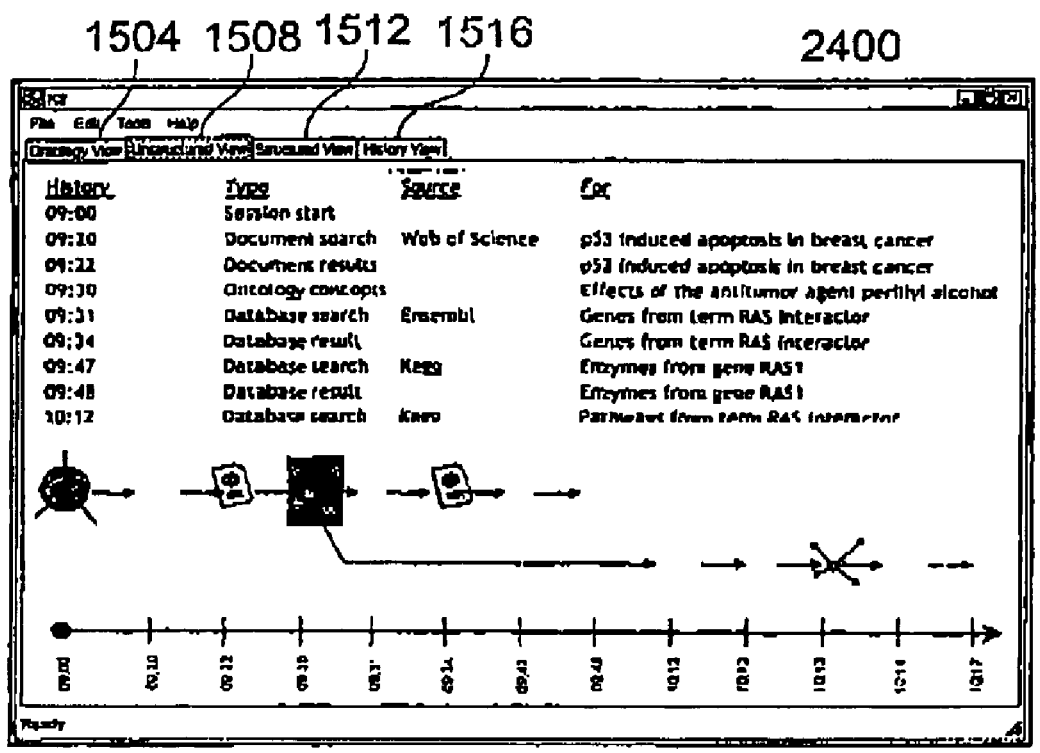
FIG. 24 illustrates an example of a session history view, according to an embodiment of the invention.

According to an embodiment of the invention shown in view 2400 of FIG. 24, the application may record a history of a user session. Examples of events may comprise document searches, database searches, ontology linking, or other events. The history may contain an event timeline, and may be made available in both tabular and graphical formats from the "history view" tab 1516.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A computer-implemented ontology-based information management system, comprising:
    a first storage means for storing structured data;
    a second storage means for storing unstructured data;
    at least one ontology;
    mapping means for mapping structured data entries stored in the first storage means and concepts in unstructured data stored in the second storage means into the at least one ontology;
    an ontology parser, including a sentence lexer for transforming input sentences into part of speech-tagged instances of concepts from the ontology, a rules-based post-lexer-filter, a parser for creating syntactic tree structure that represent grammatical relationships between the ontological concepts, based on the tags attached to the concepts, a rules-based post-parser-filter;
    searching means for accepting one or more search strings for searching against the at least one ontology and returning search results; and
    display means for displaying the returned search results.

2. The system of claim 1, wherein the first storage means for storing structured data comprises one or more proprietary databases and one or more public databases.

3. The system of claim 1, wherein the structured data comprises information from at least one of a genomic, proteomic, or chemical database.

4. The system of claim 1, wherein the second storage means for storing unstructured data comprises at least one of an intellectual property database or a scientific literature database.

5. The system of claim 1 comprising a structured query engine and unstructured information retrieval engine.

6. The system of claim 1 comprising means for recognizing user profile information and determining if search results are relevant to a user based at least in part on user profile information.

7. The system of claim 1 comprising a context-based probabilistic search engine to identify documents containing concepts relevant to query terms.

8. The system of claim 1 comprising means for inferring concepts from a group of tokens in a query.

9. The system of claim 1 comprising means for creating an inverted index of words and their position in documents.

10. The system of claim 1 comprising a means for mapping a distance between any pair of related ontology terms.

11. The system of claim 1, wherein the search results include at least one document; and further comprising:
    means for determining concepts related to the document;
    means for displaying an icon related to the document as a central display item and displaying concepts related to the document around the central display item;
    means for receiving input relating to a selected one of the displayed concepts; and
    means for generating a new display with the selected concept as a central display item and concepts related to the selected concept around the selected concept.

12. The system of claim 1, wherein the search result include a plurality of nodes, further comprising:
    means for selecting a node;
    means for causing the selected node to be in focus;
    means for displaying a node in focus as a central node and displaying related nodes around the node in focus and spacing each of the related nodes a distance from the central node, wherein the distance from a related node to the central node relates to the relevance of the related node to the central node.

13. The system of claim 12 further comprising: means for receiving a selection related to a selected node and, means for displaying properties associated with the selected node.

14. The system of claim 1 wherein the ontology comprises concept-relationship-concept triples and wherein display means comprises means for displaying a concept as a central concept and displaying related concepts connected to the central concept, wherein the connection relates to a relationship between the central concept and the central concept.

15. A computer-implemented method for managing ontology-based information, the method comprising the step of:
    storing structured data in a first storage device;
    storing unstructured data in a second storage device;
    mapping structured data entries and concepts from the unstructured data into at least one ontology;
    using an ontological parser, including a sentence lexer, for transforming input sentences into part of speech-tagged instances of concepts from the ontology;
    performing rules-based post-lexer-filtering;
    using a parser for creating syntactic tree structure that represent grammatical relationships between the ontological concepts, based on the tags attached to the concepts;
    performing a rules-based post-parser-filtering;
    receiving one or more search strings for searching against the at least one ontology;
    returning search results; and
    displaying the returned search results.

16. The method of claim 15, wherein the first storage device comprises one or more proprietary databases and one or more public databases.

17. The method of claim 15, wherein the structured data comprises information from at least one of a genomic, proteomic, or chemical database.

18. The method of claim 15, wherein the second storage device comprises one or more of an intellectual property database or a scientific literature database.

19. The method of claim 15, wherein the search results include at least one document; and further comprising the steps of:
    determining concepts related to the document;
    displaying an icon related to the document as a central display item and displaying the concepts related to the document around the central display item;
    receiving input relating to a selected one of the displayed concepts; and
    generating a new display with the selected concept as a central display item and concepts related to the selected concept around the selected concept.

20. The method of claim 15, wherein the search results include a plurality of nodes, further comprising the steps of:
    displaying a node in focus as a central node and displaying related nodes around the node in focus
    spacing each of the related nodes a distance from the central node, wherein the distance from a related node to the central node relates to the relevance of the related node to the central node.

21. The method of claim 15 further comprising the steps of receiving a selection relating to a selected node and, in response to receiving the selection, displaying properties associated with the selected node.

22. The method of claim 15 wherein the ontology comprises concept-relationship-concept triples and wherein the step of displaying comprises displaying a concept as a central concept and displaying related concepts connected to the central concept, where the connection relates to a relationship between the central concept and the central concept.

23. The method of claim 15, further comprising the step of providing a structured query engine and unstructured information retrieval engine.

24. The method of claim 15, further comprising the step of recognizing user profile information and determining if search results are relevant to a user based at least in part on user profile information.

25. The method of claim 15, further comprising the step of using a context-based probabilistic search engine to identify documents containing concepts relevant to query terms.

26. The method of claim 15, further comprising the step of mapping a distance between any pair of related ontology terms.

* * * * *